US010991463B2

(12) United States Patent
Kutzko et al.

(10) Patent No.: US 10,991,463 B2
(45) Date of Patent: *Apr. 27, 2021

(54) COMPUTER-IMPLEMENTED SYSTEM AND METHODS FOR PREDICTING THE HEALTH AND THERAPEUTIC BEHAVIOR OF INDIVIDUALS USING ARTIFICIAL INTELLIGENCE, SMART CONTRACTS AND BLOCKCHAIN

(71) Applicants: John D. Kutzko, Pagosa Springs, CO (US); Wayne C. A. Wright, Linton Maidstone KENT (GB)

(72) Inventors: John D. Kutzko, Pagosa Springs, CO (US); Wayne C. A. Wright, Linton Maidstone KENT (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/930,136

(22) Filed: May 12, 2020

(65) Prior Publication Data
US 2020/0273578 A1   Aug. 27, 2020

Related U.S. Application Data

(63) Continuation-in-part of application No. 16/415,597, filed on May 17, 2019.
(Continued)

(51) Int. Cl.
*G16H 10/60* (2018.01)
*G16H 20/00* (2018.01)
(Continued)

(52) U.S. Cl.
CPC .............. *G16H 50/30* (2018.01); *G06N 5/025* (2013.01); *G06Q 20/382* (2013.01);
(Continued)

(58) Field of Classification Search
CPC ........ G16H 50/30; G16H 10/60; G16H 20/00; G06N 5/025; H04L 9/0637; H04L 2209/38; G06Q 2220/00
See application file for complete search history.

(56) References Cited

U.S. PATENT DOCUMENTS 9,460,400 B2   10/2016   De Bruin et al.
10,340,038 B2   7/2019   Witchey
(Continued)

FOREIGN PATENT DOCUMENTS

EP   3236374   * 10/2017   .............. G06F 19/00

OTHER PUBLICATIONS

"A Blockchain-Based Smart Contract Payment System for Healthcare Management" by Asma Khatoon; Published on Jan. 3, 2020 (online).*
(Continued)

*Primary Examiner* — Vivek D Koppikar
(74) *Attorney, Agent, or Firm* — Neo IP

(57) ABSTRACT

A computer implemented method of predicting the health and therapeutic behavior of patients and making treatment plan recommendations includes the steps of: receiving patient healthcare data having one or more conditions and limiting factors; determining a therapeutic behavior pattern of patient; determining unsuccessful therapies and successful therapies for each condition based on therapeutic behavior pattern; and calculating cost quote for successful therapies based on limiting factors for time period. A computer implemented method of providing cost effective therapy for a patient is also provided and includes the steps of: receiving patient healthcare data; determining unsuccessful therapies and successful therapies; calculating probability of disease progression; calculating possible therapies ranked by probability of successful treatment; calculate cost quote for
(Continued)

possible therapies; and paying a smart contract for a selected therapy.

19 Claims, 13 Drawing Sheets

Related U.S. Application Data

(60) Provisional application No. 62/673,719, filed on May 18, 2018.

(51) Int. Cl.
| | | |
|---|---|---|
| *H04L 9/06* | (2006.01) | |
| *G06Q 20/38* | (2012.01) | |
| *G06N 5/02* | (2006.01) | |
| *G16H 50/30* | (2018.01) | |

(52) U.S. Cl.
CPC ............ *G16H 10/60* (2018.01); *G16H 20/00* (2018.01); *H04L 9/0637* (2013.01); *G06Q 2220/00* (2013.01); *H04L 2209/38* (2013.01)

(56) References Cited

U.S. PATENT DOCUMENTS

| | | | |
|---|---|---|---|
| 10,366,204 B2 | 7/2019 | Tanner et al. | |
| 10,560,272 B2 | 2/2020 | Yang et al. | |
| 2002/0095313 A1* | 7/2002 | Haq | G06F 19/3481 |
| | | | 705/2 |
| 2012/0253139 A1* | 10/2012 | Maman | G06F 19/3456 |
| | | | 600/300 |
| 2015/0100335 A1* | 4/2015 | Englehard | G06F 19/3462 |
| | | | 705/2 |
| 2016/0239636 A1* | 8/2016 | O'Donnell | G06F 19/3456 |
| 2016/0306931 A1 | 10/2016 | Lahteenmaki | |
| 2017/0169171 A1* | 6/2017 | Loeb | G06K 9/6277 |
| 2018/0060496 A1 | 3/2018 | Bulleit et al. | |
| 2018/0082030 A1 | 3/2018 | Allen et al. | |
| 2018/0165588 A1 | 6/2018 | Saxena et al. | |
| 2018/0277246 A1* | 9/2018 | Zhong | A61M 5/14212 |
| 2019/0035499 A1 | 1/2019 | Daya | |
| 2019/0163871 A1* | 5/2019 | Curbera | G06Q 20/40 |
| 2019/0198144 A1 | 6/2019 | Blackley et al. | |
| 2019/0237169 A1 | 8/2019 | Culver et al. | |
| 2019/0266597 A1 | 8/2019 | Mohtar | |
| 2019/0311791 A1 | 10/2019 | St. Paul | |
| 2019/0354693 A1* | 11/2019 | Yoon | G06F 21/6245 |
| 2019/0355472 A1 | 11/2019 | Kutzko | |
| 2019/0378094 A1 | 12/2019 | Quinn | |
| 2020/0058381 A1* | 2/2020 | Patel | G16H 10/60 |
| 2020/0082933 A1* | 3/2020 | Lu | G16H 10/60 |

OTHER PUBLICATIONS

"Blockchain in Healthcare: A Patient-Centered Model" by Hannah Chen et al,; Published on Aug. 8, 2019 (online).*

"Cryptocurrency in Healthcare" Mar. 2018 from OmnicomHealthGroup (available online).*

Blockchain, Smart Contracts, and Health: Booz Allen Hamilton and the Blockchain Revolution, by Tori Adams, published on Dec. 11, 2015 (available at www.linkedin.com).*

* cited by examiner

BLOCKCHAIN DATABASE 113

HEALTHCARE DATA 120

CONDITIONS 121

LIMITING FACTORS 122

COMPLIANCE RECORD 123

THERAPEUTIC BEHAVIOR PATTERN 124

SUCCESSFUL THERAPY 125

UNSUCCESSFUL THERAPY 126

POSSIBLE THERAPY 127

PROBABILITY OF DISEASE PROGRESSION 128

COST QUOTES 129

SUCCESSFUL PROBABILITY THRESHOLD 130

SMART CONTRACTS 131

CRYPTOCURRENCY TOKENS 132

COMPUTER-IMPLEMENTED SYSTEM AND METHODS FOR PREDICTING THE HEALTH AND THERAPEUTIC BEHAVIOR OF INDIVIDUALS USING ARTIFICIAL INTELLIGENCE, SMART CONTRACTS AND BLOCKCHAIN

CROSS REFERENCES TO RELATED APPLICATIONS

This application is related to and claims priority from the following US patents and patent applications: it is a continuation-in-part of U.S. application Ser. No. 16/415,597, filed May 17, 2019, which claims priority to and the benefit of U.S. Provisional Application No. 62/673,719, filed on May 18, 2018, each of which is incorporated herein by reference in its entirety.

BACKGROUND OF THE INVENTION

1. Field of the Invention

The present invention relates to the field of systems and methods for providing cost effective healthcare that is individually personalized.

2. Description of the Prior Art

The health of individuals taking medications is impacted by a variety of factors. These factors may include the therapeutic behavior of the medications on the individual, synergistic or antagonistic behavior of other medications taken alongside an existing medication, co-morbidities, genetics, and lifestyle behaviors, such as smoking, weight changes, medication compliance, and mental health situations. Currently, there are no systems and methods which are able to use these factors to predict changes in the one or more conditions of an individual as well as to provide a prediction to achieve a healthier lifestyle through changes in lifestyle circumstances, changes in drug types, and information on interactions with other drugs that the individual is taking. Patients and healthcare providers, such as large employers, third party administrators, governmental agencies (DoD, Tricare, Va.), pharmacy benefit managers and insurance providers, would greatly benefit from systems and methods which are operable to provide or predict the drug usage for an individual and which are also able to outline a drug usage and cost schedule for a period of time which will clearly define the healthcare needs of the individual.

Therefore, a need exists for novel computer-implemented systems and methods for providing cost effective healthcare that is individually personalized. A further need exists for novel computer-implemented systems and methods that are configured to use a plurality of patient specific factors to predict changes in the one or more conditions of an individual as well as to provide a prediction to achieve a healthier lifestyle through changes in lifestyle circumstances. There is also a need for novel computer-implemented systems and methods that are configured to provide or predict the drug usage for an individual and which are also able to outline a drug usage and cost schedule for a period of time which will clearly define the healthcare needs of the individual.

Prior art patent documents include the following:

U.S. Pat. No. 10,366,204 for System and method for decentralized autonomous healthcare economy platform by inventors Tanner, et al., filed Nov. 5, 2015 and issued Jul. 20, 2019, is directed to a system and method for a decentralized autonomous healthcare economy platform. The system and method aggregates all of the healthcare data into a global graph-theoretic topology and processes the data via a hybrid federated and peer to peer distributed processing architectures.

U.S. Patent Application No. 2019/0378094 for Data analytics framework for identifying savings opportunity for self-funded healthcare payers by inventor Quinn, filed Jun. 11, 2019 and published Dec. 12, 2019, is directed to connecting entities providing healthcare benefits with healthcare service providers without the need for third-party advisers or brokers. This allows self-funding payers to tailor their selections of healthcare services via a direct interface by applying machine-learning and/or blockchain technology to healthcare data acquired in near real-time on patient treatment plans, health insights and patient choice, patient health, and financial insights and control. It further allows the self-funding payer to perform data analytics on the acquired healthcare data to identify savings opportunity and generate a savings recipe for realizing the savings opportunity.

U.S. Patent Application No. 2018/0060496 for Blockchain-based mechanisms for secure health information exchange by inventors Bulleit, et al., filed Aug. 23, 2017 and published Mar. 1, 2018, is directed to technologies to secure flexible access to the healthcare information resources (HIR) contained within electronic health records (EHR) systems. By managing access permissions with certified self-sovereign identities and distributed ledger techniques, HIR may be secured. Patients and other users may be registered to access a distributed ledger, such as a healthcare blockchain, employed to set, host and adjudicate permissions to access HIR. Authorized owners and/or patients with rights to their own HIR may be able to grant fine-grained and conditional access permissions to third-parties. Information transfers and transactions occurring according to these permissions may be logged within smart contracts incorporated in the healthcare blockchain.

U.S. Patent Application No. 2019/0198144 for Blockchain prescription management system by inventors Blackley, et al., filed Dec. 27, 2017 and published Jun. 27, 2019, is directed to a system for managing prescriptions via a blockchain. The system records in the blockchain a prescription transaction that identifies a prescription that has been written for a patient. The system then records in the blockchain a submission selection transaction with code for controlling selection of a pharmacy to dispense the prescription. For pharmacies that provide a submission for dispensing the prescription, the system records in the blockchain a submission transaction with submission information relating to dispensing of the prescription by the pharmacy. When a pharmacy is selected to dispense the prescription, the system records in the blockchain a selected submission transaction indicating the pharmacy selected to dispense the prescription. When the prescription is dispensed, the system records in the blockchain a dispense transaction indicating that the selected pharmacy has dispensed the prescription.

U.S. Patent Application No. 2019/0311791 for System and method for patient-centric universal health recording and payment by inventor St. Paul, filed Apr. 4, 2018 and published Oct. 10, 2019, is directed to a patient-centric universal health recording and payment system which can include a synchronized server having synchronized patient information accessible and controllable by a patient, a plurality of electronic medical record databases selectively synchronized with the synchronized server, and a universal user interface for presenting the synchronized patient information including information from all accessed providers. The system can further include a plurality of third party inputs to the synchronized server selectively providing information regarding the patient, a plurality of patient sourced inputs to the synchronized server selectively providing information about the patient, and a patient input defining accessibility among and between the plurality of electronic medical record databases, a source of the plurality of third party inputs, and a source of the plurality of patient sourced inputs. The system can further include a patient health card providing patient authentication or patient identification, and funding for payments of health care services.

U.S. Patent Application No. 2019/0237169 for System for providing a data market for health data and for providing rewards to data market by inventors Culver, et al., filed Jan. 30, 2018 and published Aug. 1, 2019, is directed to a system for maintaining accurate health data and for providing rewards to data market participants. A marketplace platform based on Blockchain technology leverages smart contracts to provide rewards to sellers of data assets that provide corrections or updates to medical data, such as provider demographics. A URL API is provided to a buyer of the data with an encrypted password that is used to access the data from the URL API.

U.S. Patent Application No. 2019/0266597 for Healthcare syndicate electronic token by inventor Mohtar, filed Jan. 18, 2019 and published Aug. 29, 2019, is directed to an improved healthcare system that includes a two-tiered healthcare cryptocurrency used to digitally execute healthcare payment transactions between consumers and healthcare provides. The embodiments are directed to systems and methods for executing the healthcare payment transactions using the two-tiered healthcare cryptocurrency. The systems and methods deposit, by a healthcare service application, a sum of healthcare cryptocurrency to the healthcare service account of the user. The systems and methods receive by the user from a healthcare provider, through a user interface to the healthcare service application, a payment request for a health related service in a specified amount of the healthcare cryptocurrency. The systems and methods transmit by the user to the healthcare provider, through the user interface, a confirmation of the payment request in the specified amount. The systems and methods transfer, by the healthcare service application, the specified amount from the healthcare service account of the user to the healthcare service account of the healthcare provider. The systems and methods record, by the healthcare service application, the given health related service, the healthcare provider, and the specified amount in the blockchain.

U.S. Pat. No. 10,560,272 for Bio-information data providing method, bio-information data storing method and bio-information data transferring system based on multiple blockchains by inventors Yang, et al., filed Dec. 17, 2018 and issued Feb. 11, 2020, is directed to a method of providing bio-information data based on a plurality of blockchains. The method includes enabling a user blockchain node to store user block data including user information, a shared key, and a hash key for each user of a plurality of users, enabling an electronic contract blockchain node to store contract block data including contract information for a first user requesting a second user to generate bio-information data, the first user and the second user being included in the plurality of users, enabling a data transfer blockchain node to store transfer block data including storage information for at least one storage server that stores the bio-information data, and delivering the transfer block data from the data transfer blockchain node to the first user.

U.S. Pat. No. 10,340,038 for Healthcare transaction validation via blockchain, systems and methods by inventor Witchey, filed May 13, 2015 and issued Jul. 2, 2019, is directed to healthcare transaction validation systems and methods. Healthcare transactions associated with a stakeholder are compiled into a chain of healthcare transaction blocks. The chain can be considered a chronicle of person's healthcare path through life. When a transaction is conducted, the corresponding healthcare parameters (e.g., inputs, outputs, clinical evidence, outcomes, etc.) are sent to one or more validation devices. The devices establish a validity of the transaction and generate a new block via a proof-of-work principle. Once the new block has been calculated it can be appended to the stakeholder's health care blockchain.

U.S. Pat. No. 9,460,400 for Expert system for determining patient treatment response by inventors De Bruin, et al., filed Feb. 17, 2014 and issued Oct. 4, 2016, is directed to a medical digital expert system to predict a patient's response to a variety of treatments (using pre-treatment information). The system utilizes data fusion, advanced signal/information processing and machine learning/inference methodologies and technologies to integrate and explore diverse sets of attributes, parameters and information that are available to select the optimal treatment choice for an individual or for a subset of individuals suffering from any illness or disease including psychiatric, mental or neurological disorders and illnesses. The methodology and system can also be used to determine or confirm medical diagnosis, estimate the level, index, severity or critical medical parameters of the illness or condition, or provide a list of likely diagnoses for an individual suffering/experiencing any illness, disorder or condition.

U.S. Patent Application No. 2019/0035499 for Intelligent monitoring, interactive, and wireless internet connected medication adherence, analytics, and database solution by inventor Daya, filed Jul. 25, 2018 and published Jan. 31, 2019, is directed to a method and devices for a medication adherence platform including machine-learning analytics platform, and real-time pharmaceutical and consumer product fulfillment platform are provided. A device can comprise a sensor for sensing a medicine container or medicine, a database for storing patient related data, a computer readable medium for storing a patient treatment calendar, causing a patient's electronic device to transmit an alert based upon an event logged onto the patient treatment calendar determine medication adherence, storing data in the database, transmitting treatment-based information to the patient's device, and establishing an electronic communication channel between the patient and a healthcare professional.

U.S. Patent Application No. 2016/0306931 for Method and arrangement for arranging an information service to determine nutrition and/or medication by inventor Lahteenmaki, filed Jun. 24, 2016 and published Oct. 20, 2016, is directed to a healthcare system for personalized healthcare includes a user interface for gathering user related data of nutrition or medicaments consumed by the user, and genetic information of the user. The system also includes a research interface for gathering genetic backgrounds of different illnesses in relation to nutrition or environmental factors, and a health care practitioner interface for gathering user related data of user's health state, personalized treatment or history data. The system provides recommendations of optimal personalized nutrition or medication for the user to reach the optimal nutritive, metabolic and/or health state based on: data of nutrition or medicaments consumed by the user, genetic information of the user, genetic backgrounds of different illnesses in relation to nutrition or environmental factors, user's health state, and personalized treatment or history data of the user. The recommendations are then delivered to the user or health care practitioners via corresponding interfaces.

SUMMARY OF THE INVENTION

Computer-implemented system and methods for predicting the health and therapeutic behavior of individuals using artificial intelligence, smart contracts, and a blockchain database are provided. The system and methods disclosed herein may use a blockchain database of a blockchain network to enable a novel pharmacy benefits management healthcare model, preferably through creating Smart Healthcare contracts, to predict medication usage and spending of patients over time. In further embodiments, patients may benefit as tokenized/cryptocurrency is available for anonymized data collection and data maintenance which may eliminate copayments and coinsurances due from the patient. In still further embodiments, shared anonymized data of the system may be purchased by healthcare providers, such as pharma and health plan providers, to undergird the cryptocurrency coin/token value.

According to one embodiment consistent with the principles of the invention, a computer implemented method of predicting the health and therapeutic behavior of patients is provided. In some embodiments, the method may include the steps of: receiving healthcare data of a patient, via a client device, the healthcare data including an existing condition, a new condition, a limiting factor, and a compliance record for the existing condition; determining, via a computing device processor, a therapeutic behavior pattern of patient using the compliance record for the existing condition; determining, via the computing device processor, a successful therapy for the new condition based on the therapeutic behavior pattern; and calculating, via the computing device processor, a cost quote for the successful therapy for a time period based on the limiting factor, wherein the cost quote is operable to be a single fixed fee quote for all components of the therapy.

According to another embodiment consistent with the principles of the invention, a computer implemented method of providing cost effective therapy for a patient is provided. In some embodiments, the method may include the steps of: receiving healthcare data of a patient, via a client device, the healthcare data including a new condition; determining, via a computing device processor, at least one successful therapy for the new condition; calculating, via the computing device processor, a probability of disease progression for the new condition; determining, via the computing device processor, at least one possible therapy for the new condition; calculating, via the computing device processor, a cost quote for at least one possible therapy; and creating, via the blockchain database, a smart contract for the at least one possible therapy.

The present invention relates to individualized healthcare, and more specifically to systems and methods for providing a blockchain based treatment plan recommendation system.

It is an object of the present invention to provide a healthcare system that utilizes application whitelisting (AWL), blockchain, and cryptocurrency technologies.

It is an object of the present invention to provide a computer system that utilizes AWL, blockchain and cryptocurrency technologies that understands an individual healthcare needs and recommends alternative solutions.

It is an object of the present invention to provide a computer system that utilizes AWL, blockchain and cryptocurrency technologies that understands healthcare needs and recommends cost effective healthcare plans operable to be used by the individual or healthcare professionals.

It is an object of the present invention to provide a computer system that utilizes AWL, blockchain and cryptocurrency technologies that takes data from individuals who are experiencing similar healthcare care needs and outcomes and creates healthcare strategies (drug, lifestyle, exercise) that may improve the healthcare of all or some of those target group individuals.

It is an object of the present invention to provide a computer system that utilizes AWL, blockchain and cryptocurrency technologies that takes data from individuals who are experiencing similar healthcare needs and predicts healthcare outcomes for that individual over a fixed time period, such as 1 year.

It is an object of the present invention to provide a computer system that utilizes AWL, blockchain and cryptocurrency technologies that takes data from individuals who are experiencing similar healthcare needs and predicts healthcare outcomes for that individual over a fixed time period, such as 1 year, and works out the cost of fulfilling the healthcare needs of the individual over that period.

It is an object of the present invention to provide a computer system that utilizes AWL, blockchain and cryptocurrency technologies that takes data from individuals who are experiencing similar healthcare needs and predicts healthcare outcomes for that individual over a fixed time period, such as 1 year, and works out the cost of fulfilling the healthcare needs of the individual over that period and ensures that those costs do not increase over that period by helping the individual to follow the plan and learn to recommend solutions to improve their health. In one embodiment, additional medications are required to control the disease state, but the costs of fulfilling the healthcare needs of the individual do not change.

It is an object of the present invention to provide a computer system that utilizes AWL, blockchain and cryptocurrency technologies that incentivize individuals to improve their health through rewarding them with set health goals that are linked to smart contracts. In one embodiment, health goals comprise lab values, exam results, adherence levels, compliance, and persistence.

It is an object of the present invention to provide a computer system that utilizes AWL, blockchain and cryptocurrency technologies that takes anonymized data from patients and identifies trends and adherence behaviors of drugs and services operable to be used to improve pharmaceutical manufacturers understanding of the, efficacy, toxicity, and adherence of their drug products. Objective measures of efficacy or toxicity, as well as subjective measures of efficacy or toxicity, are operable to be direct or indirect (inverse) metrics. An objective metric is a readily measured biomarker such as blood pressure, blood glucose and serum creatinine. A subjective metric is based on clinician's impression from an interview with patient and the patient's self-reported symptoms. A direct metric is a value (either objective or subjective) that increases when the dosage of a drug is increased, and decreases when the dosage of a drug is decreased. An indirect metric is a value (either objective or subjective) that increases when the dosage of a drug is decreased, and decreases when the dosage of a drug is increased. For example, a direct objective metric of efficacy is a vancomycin serum level related to a vancomycin dose, as increase in dosage would result in increased serum level. An example of an indirect objective metric of efficacy is a blood pressure medication related to measured blood pressure, as increase in dosage would result in decreased blood pressure. An example of a direct subjective measurement of efficacy is an oral medication for Alzheimer's Disease related to cognitive improvement and patient memories, as increase in dosage would result in improved cognition and increased patient memories. An example of an indirect subjective metric of efficacy is an oral antidepressant medication dosage related to the results of Major Depression Index (MDI) scoring, as an increase in dosage would result in decreased MDI score values.

It is an object of the present invention to provide a computer system that utilizes AWL, blockchain and cryptocurrency technologies that takes anonymized data from patients around the world and helps physicians, hospital and healthcare practitioners to identify better healthcare strategies for their patients.

It is further an object of this invention to provide a system and method for improving medical treatment plan recommendations while providing patients with ownership of their own healthcare data and reducing costs and delays of the modern healthcare system.

In one embodiment, the present invention teaches a method for making artificial intelligence based medical treatment plan recommendations comprising the steps of retrieving healthcare data of a patient from a blockchain database, wherein the healthcare data comprises one or more existing conditions, one or more new conditions, one or more limiting factors, and a compliance record for the existing condition, an artificial intelligence system determining a therapeutic behavior pattern of the patient, the artificial intelligence system determining one or more therapies for the one or more new conditions based on the healthcare data of the patient, wherein the artificial intelligence system is stored on an electronic device including a processor, the artificial intelligence system determining one or more cost quotes for the one or more therapies, receiving selection of a therapy and a cost quote for the selected therapy, and the blockchain database creates a smart contract for the execution of the selected therapy.

In another embodiment, the present invention teaches a method for making artificial intelligence based medical treatment plan recommendations comprising the steps of retrieving healthcare data of a patient from a blockchain database, wherein the healthcare data comprises one or more existing conditions and one or more new conditions, an artificial intelligence system determining one or more therapies based on the healthcare data of the patient, wherein the artificial intelligence system is stored on an electronic device including a processor, the artificial intelligence system calculating a probability of disease progression for the one or more new conditions, the artificial intelligence system ranking the one or more therapies by probability of successfully treating the one or more new conditions, the artificial intelligence system determining one or more cost quotes for the one or more therapies, receiving a selection of a therapy and a cost quote for the selected therapy, the blockchain database creating a smart contract for the execution of the selected therapy, and wherein the selected therapy is paid for with a native cryptocurrency or another security token, utility token, or fiat currency.

In yet another embodiment, the present invention teaches a system for making artificial intelligence based medical treatment plan recommendations comprising an electronic device including a processor and an artificial intelligence system, and a blockchain database including healthcare data of a patient, wherein the healthcare data of a patient includes at least one conditions, wherein the artificial intelligence system receives the healthcare data of the patient and determines at least one therapy for the at least one condition, wherein the artificial intelligence system calculates a probability of disease progression for the at least one conditions, wherein the artificial intelligence system determines at least one cost quote for the at least one therapy, and wherein the blockchain database creates at least one smart contract for the at least one therapy.

These and other aspects of the present invention will become apparent to those skilled in the art after a reading of the following description of the preferred embodiment when considered with the drawings, as they support the claimed invention.

BRIEF DESCRIPTION OF THE DRAWINGS

FIG. 4B shows a block diagram illustrating some components of a blockchain database according to various embodiments described herein

FIG. 7A illustrates a patient dashboard providing access to all health information, according to one embodiment of the present invention.

DETAILED DESCRIPTION

Figure 1:
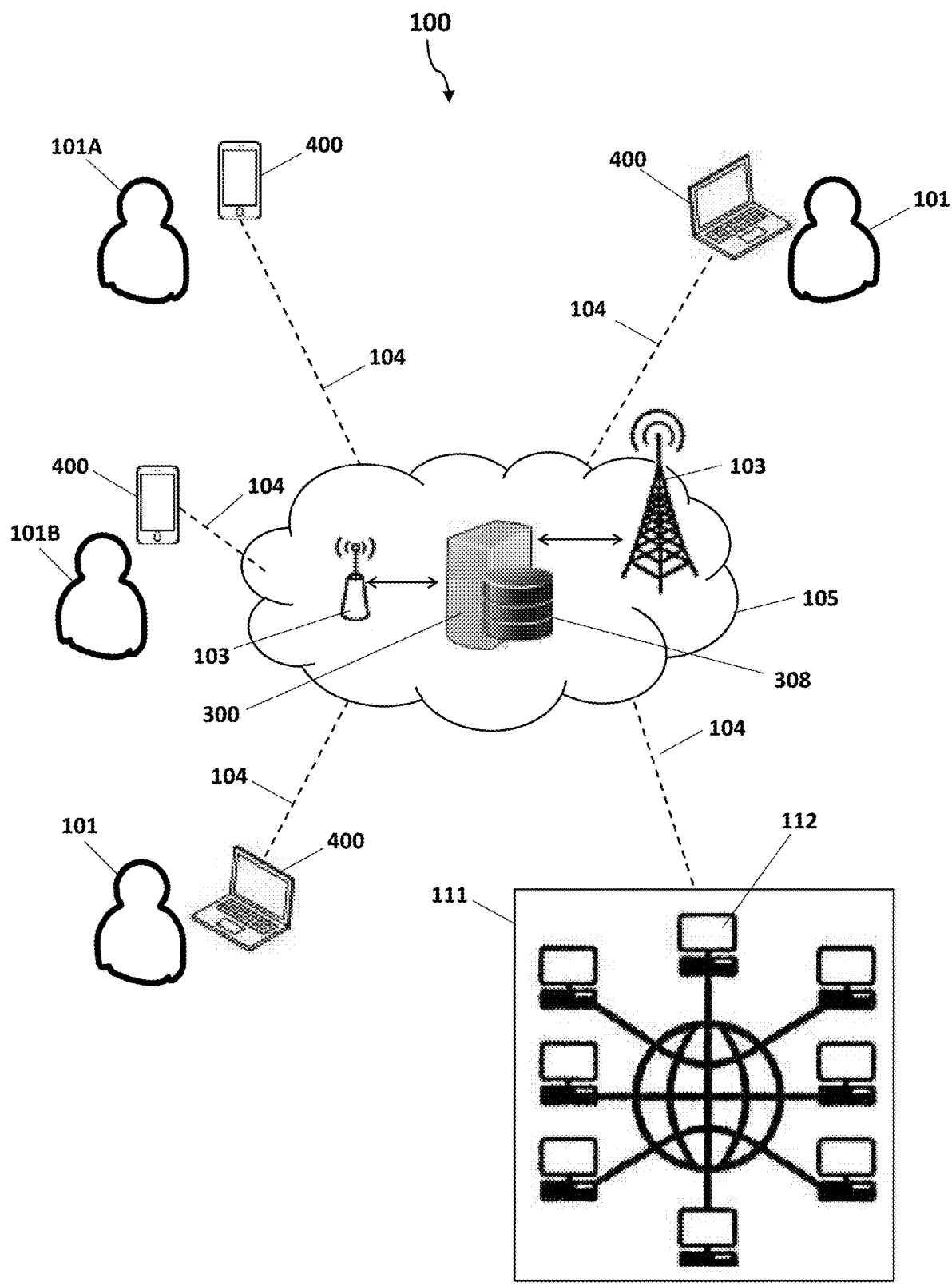
FIG. 1 depicts an illustrative example of some of the components and computer implemented methods which may be found in a system for predicting the health and therapeutic behavior of individuals according to various embodiments described herein.

The present invention is generally directed to individualized healthcare, and more specifically to systems and methods for providing a blockchain based treatment plan recommendation system.

In one embodiment, the present invention teaches a method for making artificial intelligence based medical treatment plan recommendations comprising the steps of retrieving healthcare data of a patient from a blockchain database, wherein the healthcare data comprises one or more existing conditions, one or more new conditions, one or more limiting factors, and a compliance record for the existing condition, an artificial intelligence system determining a therapeutic behavior pattern of the patient, the artificial intelligence system determining one or more therapies for the one or more new conditions and/or one or more existing conditions based on the healthcare data of the patient, wherein the artificial intelligence system is stored on an electronic device including a processor, the artificial intelligence system determining one or more cost quotes for the one or more therapies, receiving selection of a therapy and a cost quote for the selected therapy, and the blockchain database creating a smart contract for the execution of the selected therapy.

In another embodiment, the present invention teaches a method for making artificial intelligence based medical treatment plan recommendations comprising the steps of retrieving healthcare data of a patient from a blockchain database, wherein the healthcare data comprises one or more existing conditions and one or more new conditions, an artificial intelligence system determining one or more therapies based on the healthcare data of the patient, wherein the artificial intelligence system is stored on an electronic device including a processor, the artificial intelligence system calculating a probability of disease progression for the one or more new conditions and/or one or more existing conditions, the artificial intelligence system ranking the one or more therapies by probability of successfully treating the one or more new conditions and/or one or more existing conditions, the artificial intelligence system determining one or more cost quotes for the one or more therapies, receiving a selection of a therapy and a cost quote for the selected therapy, the blockchain database creating a smart contract for the execution of the selected therapy, and wherein the selected therapy is paid for with a native cryptocurrency.

None of the prior art discloses a system which provides medical treatment plan recommendations using artificial intelligence taught by health information stored on the blockchain.

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Although the terms "first", "second", etc. are used herein to describe various elements, these elements should not be limited by these terms. These terms are only used to distinguish one element from another element. For example, the first element may be designated as the second element, and the second element may be likewise designated as the first element without departing from the scope of the invention.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

Definitions

As used herein, the term "Patient" may refer to a person or animal under healthcare. The person or animal may be waiting for this care or may be receiving it or may have already received it. Examples of the definition of patient include; a person or animal who requires medical care; a person or animal receiving medical or dental care or treatment; a person or animal under a physician's or veterinarian's care for a particular disease or condition; a person or animal who is waiting for or undergoing medical treatment and care; and an individual or animal who is receiving needed professional services that are directed by a licensed practitioner of the healing arts toward maintenance, improvement or protection of health or lessening of illness, disability or pain. (US Centers for Medicare & Medicaid Services).

As used herein, the term "Prescription Drug" may refer to The Federal Food Drug and Cosmetic Act (FD&C Act) and FDA regulations which define the term drug, in part, by reference to its intended use, as "articles intended for use in the diagnosis, cure, mitigation, treatment, or prevention of disease" and "articles (other than food) intended to affect the structure or any function of the body of man or other animals." Therefore, almost any ingested or topical or injectable product that, through its label or labeling (including internet websites, promotional pamphlets, and other marketing material), is claimed to be beneficial for such uses will be regulated by FDA as a drug. The definition also includes components of drugs, such as active pharmaceutical ingredients, and 3d-printed medications with either singe active pharmaceutical ingredients or multiple pharmaceutical ingredients. Prescription drugs are also operable to include compounds which are not FDA approved, and drugs used for an indication which they are not FDA approved, such as those that fall into National Comprehensive Cancer Network (NCCN) guidelines, other guidelines, or appear in peer-reviewed journal articles.

As used herein, the term "Drug Compounding" may refer to the preparation, mixing, assembling, altering, packaging and labelling of a drug, drug-delivery device or device in accordance with a license practitioner's prescription, medication order, or initiative based on the practitioner/patient/pharmacist/compounder relationship in the course of professional practice. This may include customizations which may include: Different Form or Method of Delivery; Custom Strength or Dose; Combine Medications; Allergies or Intolerance to Components of FDA-Approved Drugs; Medications Not Available Commercially; Bioidentical Hormone Replacement; Flavoring As used herein, the term "Veterinary Prescription Drugs" may refer to Veterinary prescription drugs are those drugs restricted by federal law to use by or on the order of a licensed veterinarian for use in an animal [Section 503(f) Food, Drug, and Cosmetic Act]. The law requires that the drug sponsor label such drugs with the statement: "Caution: Federal law restricts this drug to use by or on the order of a licensed veterinarian." Veterinary prescription drugs are labeled for use only by or on the order of a licensed veterinarian. Veterinarians making treatment decisions must use sound clinical judgment and current medical information and must be in compliance with federal, state, and local laws and regulations. Veterinary prescription drugs must be properly labeled before being dispensed. Appropriate dispensing and treatment records must be maintained. Veterinary prescription drugs should be dispensed only in quantities required for the treatment of the animal(s) for which the drugs are dispensed. Avoid unlimited refills of prescriptions or any other activity that might result in misuse of drugs. Any drug used in a manner not in accordance with its labeling should be subjected to the same supervisory precautions that apply to veterinary prescription drugs. Orders issued by licensed veterinarians authorize drug distributors to deliver veterinary prescription drugs to a specific client, or authorize pharmacists to dispense such drugs to a specific client.

As used herein, the term "Specialty Pharmacy" may refer to a specialty pharmacy is a state-licensed pharmacy that solely or largely provides only medications for people with serious health conditions requiring complex therapies. These include conditions such as, but not limited to, cancer, hepatitis C, rheumatoid arthritis, HIV/AIDS, multiple sclerosis, cystic fibrosis, organ transplantation, human growth hormone deficiencies, hemophilia and other bleeding disorders, addiction and addiction management, asthma, allergies, cardiovascular diseases, dermatological conditions, endocrinology, fertility, gastrointestinal diseases and Crohn's disease, Immune Globulin deficiencies, ophthalmology, chronic pain management, rheumatology, respiratory syncytial virus, COVID-19, transplantation, and urology. In addition to being state-licensed and regulated, specialty pharmacies are typically accredited by independent third parties such as URAC®, the Accreditation Commission for Health Care (ACHC), the Center for Pharmacy Practice Accreditation (CPPA) or the Joint Commission, in order to ensure consistent quality of care.

Specialty medications have a complex profile that require intensive patient management. Some specialty medications also require special handling. Though some are taken orally, many of these medications need to be injected or infused, some in a doctor's office or hospital. Specialty pharmacies provide services that include training in how to use these medications, comprehensive treatment assessment, patient monitoring, and frequent communication with caregivers and the patient's physician or other healthcare providers. The expert services that specialty pharmacies provide drive adherence and persistency, proper management of medication dosing and side effects, and ensure appropriate medication use.

Specialty drugs are more complex than most prescription medications and are used to treat patients with serious and often life-threatening conditions including and related to, but not limited to, cancer, hepatitis C, rheumatoid arthritis, HIV/AIDS, multiple sclerosis, cystic fibrosis, organ transplantation, human growth hormone deficiencies, hemophilia and other bleeding disorders, addiction and addiction management, asthma, allergies, cardiovascular diseases, dermatological conditions, endocrinology, fertility, gastrointestinal diseases and Crohn's disease, Immune Globulin deficiencies, ophthalmology, chronic pain management, rheumatology, respiratory syncytial virus, COVID-19, transplantation, and urology. The complexity of these medications may be due to the drug itself, the way it is administered, the management of its side effect profile, the disease or condition it is used to treat, special access conditions required by the manufacturer, payer authorization or benefit requirements, patient financial hardship or any combination of these.

As used herein, the term "Medical *Cannabis*" may refer to any type of *cannabis*, although *cannabis* remains federally illegal in the United States, many states have legalized *cannabis* for valid medical purposes (and several states have legalized *cannabis* both medically and for adult use). In order to qualify for medical marijuana, patients must have a diagnosed ailment that is on their state's list of qualifying medical marijuana conditions. With the recommendation of a local physician, a qualified patient is able to obtain a medical marijuana card or authorization to visit dispensaries and purchase medical marijuana products. (In states where recreational *cannabis* has been legalized, adult consumers do not need a medical marijuana card, but may not have access to the same medical *cannabis* products that are available for patients.)

Medical *cannabis* refers to using the whole *cannabis* plant, or the plant's basic extracts, for the treatment of various ailments or conditions. The characteristic that defines marijuana from hemp is the content of tetrahydrocannabinol (THC), the compound in *cannabis* that gets users "high." Hemp is almost entirely devoid of THC but often high in another cannabinoid-cannabidiol (CBD). Hemp has 0.3 percent THC or less while the threshold for marijuana starts at a THC concentration of 0.31 percent or higher. Both forms of *cannabis*, hemp and marijuana, have been shown to contain medically beneficial levels of differing cannabinoids, active compounds found in the *cannabis* plant.

Medical *cannabis* encompasses synthetic and non-synthetic (naturally occurring) cannabinoids.

Non-Synthetic (naturally occurring) *cannabis* includes over 120 cannabinoids, some of which have been found to have therapeutically beneficial properties. The two major cannabinoids found in *cannabis* that academic and scientific studies demonstrate to possess the most therapeutic properties are cannabidiol (CBD) and tetrahydrocannabinol (THC), though a number of other cannabinoids, like cannabigerol (CBG) and cannabinol (CBN), also exhibit health benefits.

These cannabinoids interact directly with the body's endocannabinoid system—a signaling network found within every mammalian species on Earth. It features two main cannabinoid receptors, CB1 and CB2 receptors, which THC and CBD "dock" with to provide their therapeutic effects. Additional cannabinoid receptors include CB3, CB4, CB5, GPR55, GPR119, GPR18, GABA, and serotonin and have been implicated as novel cannabinoid receptors in the endocannabinoid system. THC, the mind-altering ingredient in *cannabis*, has been shown to increase appetite, reduce muscle control problems, and reduce nausea, pain, and inflammation. CBD doesn't cause a psychoactive effect like THC, but it has been shown to reduce pain and inflammation, as well as be effective in killing certain cancer cells, controlling epileptic seizures, and treating mental illness.

Additional phytocannabinoids include cannabigerolic acid (CBGA), tetrahydrocannabinolic acid (THCA), cannabidiolic acid (CBDA), cannabichromenic acid (CBCA), cannabigerolic acid (CBGA), tetrahydrocannabivarin carboxylic acid (THCVA), cannabidivarinic acid (CBDVA), cannabichromevarinic acid (CBCVA), CBG, THC, CBD, cannabichromene (CBC), cannabigerovarin (CBGV), tetrahydrocannabivarin (THCV), cannabidivarin (CBDV), and cannabichromevarin (CBCV).

As used herein, the term "Clinical Laboratory Tests" may refer to a medical procedure that involves testing a sample of blood, urine, or other substance from the body. Laboratory tests are able to help determine a diagnosis, plan treatment, check to see if treatment is working, or monitor the disease over time.

A clinical (medical) laboratory is a facility that performs testing on materials derived from the human body for the purpose of providing information for the diagnosis, prevention, or treatment of any disease or impairment of, or assessment of the health of, human beings.

Coding for clinical laboratory tests include NCD (National Coverage Determination), ICD-10-CM, HCPCS and CPT codes.

As used herein, the term "Medical Device' may be defined within the Food Drug & Cosmetic Act as an instrument, apparatus, implement, machine, contrivance, implant, in vitro reagent, or other similar or related article, including a component part, or accessory which is: recognized in the official National Formulary, or the United States Pharmacopoeia, or any supplement to them, intended for use in the diagnosis of disease or other conditions, or in the cure, mitigation, treatment, or prevention of disease, in man or other animals, or intended to affect the structure or any function of the body of man or other animals, and which does not achieve any of its primary intended purposes through chemical action within or on the body of man or other animals and which is not dependent upon being metabolized for the achievement of any of its primary intended purposes.

Coding for medical devices includes ICD-10-PCS, CPT and HCPCS

As used herein, the term "Digital Health" may refer to the broad scope of digital health includes categories such as mobile health medical apps (mHealth), health information technology (IT), wireless medical devices, wearable medical devices, telehealth and telemedicine, software as a Medical Device (SaMD), personalized medicine, and Food and Drug Administration approved mobile health applications.

As used herein, the term "computer" refers to a machine, apparatus, or device that is capable of accepting and performing logic operations from software code. The term "application", "software", "software code" or "computer software" refers to any set of instructions operable to cause a computer to perform an operation. Software code may be operated on by a "rules engine" or processor. Thus, the methods and systems of the present invention may be performed by a computer or computing device having a processor based on instructions received by computer applications and software.

The term "electronic device" as used herein is a type of computer comprising circuitry and configured to generally perform functions such as recording audio, photos, and videos; displaying or reproducing audio, photos, and videos; storing, retrieving, or manipulation of electronic data; providing electrical communications and network connectivity; or any other similar function. Non-limiting examples of electronic devices include: personal computers (PCs), workstations, laptops, tablet PCs including the iPad, cell phones including iOS phones made by Apple Inc., Android OS phones, Microsoft OS phones, Blackberry phones, digital music players, or any electronic device capable of running computer software and displaying information to a user, memory cards, other memory storage devices, digital cameras, external battery packs, external charging devices, and the like. Certain types of electronic devices which are portable and easily carried by a person from one location to another may sometimes be referred to as a "portable electronic device" or "portable device". Some non-limiting examples of portable devices include: cell phones, smartphones, tablet computers, laptop computers, wearable computers such as Apple Watch, other smartwatches, Fitbit, other wearable fitness trackers, Google Glasses, and the like.

The term "client device" as used herein is a type of computer or computing device comprising circuitry and configured to generally perform functions such as recording audio, photos, and videos; displaying or reproducing audio, photos, and videos; storing, retrieving, or manipulation of electronic data; providing electrical communications and network connectivity; or any other similar function. Non-limiting examples of client devices include: personal computers (PCs), workstations, laptops, tablet PCs including the iPad, cell phones including iOS phones made by Apple Inc., Android OS phones, Microsoft OS phones, Blackberry phones, Apple iPads, Anota digital pens, digital music players, or any electronic device capable of running computer software and displaying information to a user, memory cards, other memory storage devices, digital cameras, external battery packs, external charging devices, and the like. Certain types of electronic devices which are portable and easily carried by a person from one location to another may sometimes be referred to as a "portable electronic device" or "portable device". Some non-limiting examples of portable devices include: cell phones, smartphones, tablet computers, laptop computers, tablets, digital pens, wearable computers such as Apple Watch, other smartwatches, Fitbit, other wearable fitness trackers, Google Glasses, other smart glasses, and the like.

The term "computer readable medium" as used herein refers to any medium that participates in providing instructions to the processor for execution. A computer readable medium may take many forms, including but not limited to, non-volatile media, volatile media, and transmission media. Non-volatile media includes, for example, optical, magnetic disks, and magneto-optical disks, such as the hard disk or the removable media drive. Volatile media includes dynamic memory, such as the main memory. Transmission media includes coaxial cables, copper wire and fiber optics, including the wires that make up the bus. Transmission media may also take the form of acoustic or light waves, such as those generated during radio wave and infrared data communications.

As used herein the term "data network" or "network" shall mean an infrastructure capable of connecting two or more computers such as client devices either using wires or wirelessly allowing them to transmit and receive data. Non-limiting examples of data networks may include the internet or wireless networks or (i.e. a "wireless network") which may include Wifi and cellular networks. For example, a network may include a local area network (LAN), a wide area network (WAN) (e.g., the Internet), a mobile relay network, a metropolitan area network (MAN), an ad hoc network, a telephone network (e.g., a Public Switched Telephone Network (PSTN)), a cellular network, a Zigby network, or a voice-over-IP (VoIP) network.

As used herein, the term "database" shall generally mean a digital collection of data or information. The present invention uses novel methods and processes to store, link, and modify information such digital images and videos and user profile information. For the purposes of the present disclosure, a database may be stored on a remote server and accessed by a client device through the internet (i.e., the database is in the cloud) or alternatively in some embodiments the database may be stored on the client device or remote computer itself (i.e., local storage). A "data store" as used herein may contain or comprise a database (i.e. information and data from a database may be recorded into a medium on a data store).

As used herein, the term "blockchain" shall generally mean a distributed database that maintains a continuously growing ledger or list of records, called blocks, secured from tampering and revision using hashes. Every time data may be published to a blockchain database the data may be published as a new block. Each block may include a timestamp and a link to a previous block. Through the use of a peer-to-peer network and a distributed timestamping server, a blockchain database is managed autonomously. Blockchains are an open, distributed ledger that are able to record transactions between two parties efficiently and in a verifiable and permanent way. Consensus ensures that the shared ledgers are exact copies, and lowers the risk of fraudulent transactions, because tampering would have to occur across many places at exactly the same time. Cryptographic hashes, such as the SHA256 computational algorithm, ensure that any alteration to transaction input results in a different hash value being computed, which indicates potentially compromised transaction input. Digital signatures ensure that transactions originated from senders (signed with private keys) and not imposters. This covers different approaches to the processing including hash trees and hash graphs. At its core, a blockchain system records the chronological order of transactions with all nodes agreeing to the validity of transactions using the chosen consensus model. The result is transactions that are irreversible and agreed to by all members in the network.

As used herein, the term application whitelisting (AWL) refers to a secure method of executing applications on a network and managing and controlling network resources.

As used herein, the term "artificial intelligence" shall generally mean smart machines capable of performing tasks that typically require human intelligence and the machines learning from experience, adjusting to new inputs, processing large amounts of data, and recognizing patterns in the data.

As used herein, the term "machine learning" shall generally mean smart machines using statistics to find patterns in large amounts of data, wherein the data is anything that can be digitally stored. Machine learning is seen as a subset of artificial intelligence, and machine learning algorithms make predictions based on data without being programmed to specifically do so.

As used herein, the term "deep learning" shall generally mean taking a range of data available from real life and researching it to suggest outcomes. In the present invention, this means predicting modification of existing drug dosages or schedules, new drugs or drug regimens, or ancillary treatments based on the individual's unique personal response, demographics and social circumstances. Generally based on artificial neural networks, deep learning utilizes multiple layers to progressively extract higher level features from the raw data input.

As used herein, the term "health condition" relates to any disease state which possesses a Clinical Modification (ICD-10-CM) code.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each is able to also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

New computer-implemented systems and methods for providing cost effective healthcare that is individually personalized. In the following description, for purposes of explanation, numerous specific details are set forth in order to provide a thorough understanding of the present invention. It will be evident, however, to one skilled in the art that the present invention may be practiced without these specific details.

The present invention is operable to be used in any healthcare organization or system, including, but not limited to, single-payer healthcare systems such as the Beveridge model, the Bismarck model and a National Health Insurance model, a private insurance or out-of-pocket system such as presently used in the United States of America, and combinations thereof. The present invention is further operable to be used with any specific type of insurance or policy, including health savings accounts (HSA), health maintenance organizations (HMO), preferred provider organizations (PPO), exclusive provider organizations (EPO), point-of-service (POS) plans, Medicare, Medicaid, Tricare, the Veteran's Administration, employer provided coverage, cash pay models (self-pay), workers' compensation models, and healthcare cost sharing models (such as Medi-Share). As used herein, workers' compensation models are a form of insurance which provides wage replacement and related medical benefits to individuals who have been injured at work and are provided in exchange for the individual's relinquishment of their right to sue the employer for the tor of negligence. Provisions in workers' compensation plans are operable to include periodic (e.g. weekly) payments in replace of wages, reimbursement or payment of medical expenses, compensation for economic loses, and benefits payable in the event of death.

Referring now to the drawings in general, the illustrations are for the purpose of describing one or more preferred embodiments of the invention and are not intended to limit the invention thereto.

The present invention will now be described by example and through referencing the appended figures representing preferred and alternative embodiments. As perhaps best shown by FIG. 1, an illustrative example of some of the physical components which may comprise a system for predicting the health and therapeutic behavior of individuals ("the system") 100 according to some embodiments is presented. The system 100 is configured to facilitate the transfer of data and information between one or more access points 103, client devices 400, and servers 300 over a data network 105. Each client device 400 may send data to and receive data from the data network 105 through a network connection 104 with an access point 103. A data store 308 accessible by the server 300 may contain one or more databases. The data may comprise any type of information pertinent to one or more users 101. In preferred embodiments, the data may include healthcare information, such as information on or describing one or more users 101, information on or describing one or more medical conditions 121, information on or describing one or more medications and other therapies used to treat medical conditions 121, information on or describing the cost of one or more medications and other therapies used to treat medical conditions 121, information requested by one or more users 101, information supplied by one or more users 101, and any other information which may be used to provide cost effective healthcare that is individually personalized.

In this example, the system 100 comprises at least one client device 400 (but preferably more than two client devices 400) configured to be operated by one or more users 101. Client devices 400 are operable to be mobile devices, such as laptops, tablet computers, personal digital assistants, smart phones, and the like, that are equipped with a wireless network interface capable of sending data to one or more servers 300 with access to one or more data stores 308 over a network 105 such as a wireless local area network (WLAN). Additionally, client devices 400 are operable to be fixed devices, such as desktops, workstations, and the like, that are equipped with a wireless or wired network interface capable of sending data to one or more servers 300 with access to one or more data stores 308 over a wireless or wired local area network 105. In another embodiment, client devices 400 include any device which produces healthcare data. The present invention may be implemented on at least one client device 400 and/or server 300 programmed to perform one or more of the steps described herein. In some embodiments, more than one client device 400 and/or server 300 may be used, with each being programmed to carry out one or more steps of a method or process described herein.

In some embodiments, the system 100 may be configured to facilitate the communication of information to and from one or more users 101, through their respective client devices 400, and servers 300 of the system 100. Users 101 of the system 100 may include one or more healthcare providers ("providers") 101A and healthcare patients ("patients") 101B. A provider 101A may include a person, company, or other entity which may provide, authorize, or pay for healthcare services and therapies for a patient 101A. Example providers 101A may include, pharmacies, pharmacists, health insurance companies, doctors, nurses, physician's assistants, anesthesiologists, other specialists, hospitals, clinics, other healthcare entities, and the like. A patient 101B may include a person that has or will receive healthcare services and one or more therapies for a health condition 121, optionally under the care of an authorized agent, such as a family member or guardian.

In one embodiment, health condition 121 is operable to be one or more of diabetes, hypertension or high blood pressure, congestive heart failure (CHF), chronic obstructive pulmonary disease (COPD), cancers including leukemias carcinomas, sarcomas, melanomas, lymphomas or any other cancer, solid tumor, or liquid tumor including all hematological malignancies, chronic kidney disease (CKD), nephritis, nephrosis, cardiovascular diseases including, but not limited to, heart rhythm disorders, valvular diseases, coronary heart disease, or stroke, hyperlipidemia, pulmonary circulation disorders, peripheral vascular disorders, renal disease or failure, overweight or obesity, neurological disorders and conditions such as depression, anxiety, attention deficit disorder (ADD), attention deficit hyperactivity disorder (ADHD), bipolar disorder, panic disorder, eating disorders, schizophrenia, autism spectrum disorder, Alzheimer's disease, and personality disorders, paralysis, hypothyroidism, hyperthyroidism, liver disease, HIV/AIDS, rheumatoid arthritis, osteoarthritis, anemia, alcohol abuse, drug abuse, solid tumor(s), fluid and electrolyte disorders, epilepsy, nonalcoholic fatty liver disease, sleep apnea, gastrointestinal disturbances, pneumonia, pulmonary embolism, skin conditions such as athlete's foot, eczema, acne, shingles, hives, sunburn, contact dermatitis, rosacea, psoriasis, cellulitis, and measles, asthma, hypocholesteremia, hypercholesteremia, fragile X syndrome, allergies such as penicillin allergy, influenza A, influenza B, injuries or conditions wherein a steroid is prescribed, sexually transmitted diseases and infections including chlamydia, syphilis, gonorrhea, *Mycoplasma genitalium*, trichomoniasis, Human Papilloma Virus (HPV), and herpes, urinary tract infection, food poisoning, hepatitis A, hepatitis B, hepatitis C, staph bacteria, COVID-19, addiction and addiction management, dermatological conditions, fertility conditions, endocrinological conditions, gastrointestinal disease and Chron's disease, Immune Globulin deficiencies, multiple sclerosis, ophthalmological conditions, chronic pain management, rheumatological conditions, respiratory syncytial virus, transplantation, urological conditions, and any other disease or condition which is operable to be medicated, treated, or managed.

In some embodiments, the system 100 may include a blockchain network 111, having one or more nodes 112, which may be in communication with one or more servers 300 and/or client devices 400 of the system 100. A node 112 may be a server 300, a client device 400, or any other suitable networked computing platform. The blockchain network 111 may manage a distributed blockchain database 113 containing healthcare information of the system 100. The healthcare information may be maintained as a continuously growing ledger or listing of the data which may be referred to as blocks, secured from tampering and revision. Each block includes a timestamp and a link to a previous block. Through the use of a peer-to-peer blockchain network 111 and a distributed timestamping server 300, a blockchain database 113 may be managed autonomously. Consensus ensures that the shared ledgers are exact copies, and lowers the risk of fraudulent transactions, because tampering would have to occur across many places at exactly the same time. Cryptographic hashes, such as the SHA256 computational algorithm, ensure that any alteration to transaction data input results in a different hash value being computed, which indicates potentially compromised transaction input. Digital signatures ensure that data entry transactions (data added to the blockchain database 113) originated from senders (signed with private keys) and not imposters. At its core, a blockchain database 113 may record the chronological order of data entry transactions with all nodes 112 agreeing to the validity of entry transactions using the chosen consensus model. The result is data entry transactions that are irreversible and agreed to by all members in the blockchain network 111.

In one embodiment of the present invention, the blockchain network 111 includes a cryptocurrency or digital asset designed to work as a medium of exchange that uses cryptography to secure its transactions, to control the creation of additional units, and to verify the transfer of assets. Example cryptocurrencies include Bitcoin, Ethereum, Ripple, etc. The blockchain network 111 may also comprise tokens 132 common to cryptocurrency based blockchain networks 111. The tokens 132 may serve as a reward or incentive to nodes 112 for blockchain network 111 services and to make the blockchain network 111 attack resistant. The blockchain network 111 may comprise token governance rulesets based on crypto economic incentive mechanisms that determine under which circumstances blockchain network 111 transactions are validated and new blocks are created. Tokens 132 may include usage tokens, work tokens, Intrinsic, Native or Built-in tokens, application token, asset-backed tokens, or any other type of token which may be used in a cryptocurrency network. The blockchain-based cryptocurrency token is able to be traded, is used to buy drugs and other non-drug products and services, and is able to be transferred to support the healthcare costs of individuals who are less fortunate. In one embodiment the token 132 is ERC-20, which is a technical standard used for all smart contracts on the Ethereum blockchain for token implementation.

In preferred embodiments, the system 100 and methods disclosed herein may use the blockchain database 113 of the blockchain network 111 to enable a novel pharmacy benefits management healthcare model, preferably through creating Smart Healthcare contracts, to predict medication usage and spending of patients 101B over time. In one embodiment, predicted mediation usage and spending of patients over time is based on factors including, but not limited to, demographics, genomics, genetics, disease, comorbidities, past therapies, and current therapies. In further embodiments, patients 101B may benefit as tokenized/cryptocurrency is available for anonymized data collection and data maintenance which may eliminate copayments and coinsurances due from the patient 101B, such that the healthcare data 120 of one or more patients 101B may be associated with cryptocurrency token(s) 132 of the system 100. In still further embodiments, shared anonymized data of the system may be purchased by healthcare providers 101A, such as pharma and health plan providers, to undergird the cryptocurrency coin/token 132 value. In preferred embodiments, all or portions of one or more third-party cryptocurrency tokens 132 may be used as payment for a patient 101B to receive one or more therapies, such as a possible therapy 127.

Figure 2:
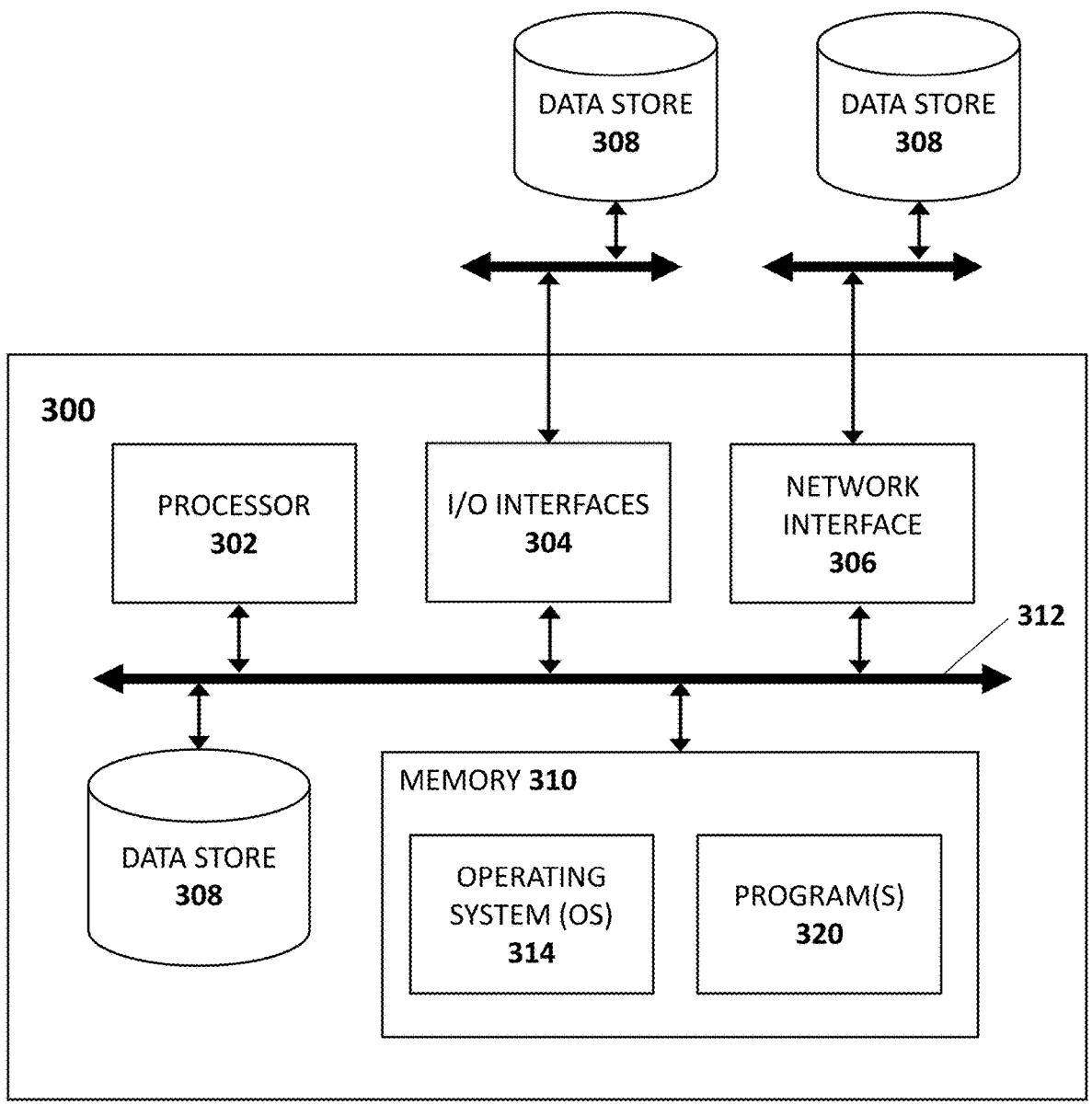
FIG. 2 illustrates a block diagram showing an example of a server which may be used by the system as described in various embodiments herein.

Referring now to FIG. 2, in an exemplary embodiment, a block diagram illustrates a server 300 of which one or more may be used in the system 100 or standalone and which may be a type of computing platform. The server 300 may be a digital computer that, in terms of hardware architecture, generally includes a processor 302, input/output (I/O) interfaces 304, a network interface 306, a data store 308, and memory 310. It should be appreciated by those of ordinary skill in the art that FIG. 2 depicts the server 300 in an oversimplified manner, and a practical embodiment may include additional components and suitably configured processing logic to support known or conventional operating features that are not described in detail herein. The components (302, 304, 306, 308, and 310) are communicatively coupled via a local interface 312. The local interface 312 may be, for example but not limited to, one or more buses or other wired or wireless connections, as is known in the art. The local interface 312 may have additional elements, which are omitted for simplicity, such as controllers, buffers (caches), drivers, repeaters, and receivers, among many others, to enable communications. Further, the local interface 312 may include address, control, and/or data connections to enable appropriate communications among the aforementioned components.

The processor 302 is a hardware device for executing software instructions. The processor 302 may be any custom made or commercially available processor, a central processing unit (CPU), an auxiliary processor among several processors associated with the server 300, a semiconductor-based microprocessor (in the form of a microchip or chip set), or generally any device for executing software instructions. When the server 300 is in operation, the processor 302 is configured to execute software stored within the memory 310, to communicate data to and from the memory 310, and to generally control operations of the server 300 pursuant to the software instructions. The I/O interfaces 304 may be used to receive user input from and/or for providing system output to one or more devices or components. User input may be provided via, for example, a keyboard, touch pad, and/or a mouse. System output may be provided via a display device and a printer (not shown). I/O interfaces 304 may include, for example, but not limited to, a serial port, a parallel port, a small computer system interface (SCSI), a serial ATA (SATA), a fibre channel, Infiniband, iSCSI, a PCI Express interface (PCI-x), an infrared (IR) interface, a radio frequency (RF) interface, and/or a universal serial bus (USB) interface.

The network interface 306 may be used to enable the server 300 to communicate on a network, such as the Internet, the data network 105, the enterprise, and the like, etc. The network interface 306 may include, for example, an Ethernet card or adapter (e.g., 10 BaseT, Fast Ethernet, Gigabit Ethernet, 10 GbE) or a wireless local area network (WLAN) card or adapter (e.g., 802.11a/b/g/n). The network interface 306 may include address, control, and/or data connections to enable appropriate communications on the network. A data store 308 may be used to store data.

The data store 308 is a type of memory and may include any of volatile memory elements (e.g., random access memory (RAM, such as DRAM, SRAM, SDRAM, and the like)), nonvolatile memory elements (e.g., ROM, hard drive, tape, CDROM, and the like), and combinations thereof. Moreover, the data store 308 may incorporate electronic, magnetic, optical, and/or other types of storage media. In one example, the data store 308 may be located internal to the server 300 such as, for example, an internal hard drive connected to the local interface 312 in the server 300. Additionally in another embodiment, the data store 308 may be located external to the server 300 such as, for example, an external hard drive connected to the I/O interfaces 304 (e.g., SCSI or USB connection). In a further embodiment, the data store 308 may be connected to the server 300 through a network, such as, for example, a network attached file server.

The memory 310 may include any of volatile memory elements (e.g., random access memory (RAM, such as DRAM, SRAM, SDRAM, etc.)), nonvolatile memory elements (e.g., ROM, hard drive, tape, CDROM, etc.), and combinations thereof. Moreover, the memory 310 may incorporate electronic, magnetic, optical, and/or other types of storage media. Note that the memory 310 may have a distributed architecture, where various components are situated remotely from one another, but are able to be accessed by the processor 302. The software in memory 310 may include one or more software programs, each of which includes an ordered listing of executable instructions for implementing logical functions. The software in the memory 310 may include a suitable operating system (O/S) 314 and one or more programs 320.

The operating system 314 essentially controls the execution of other computer programs, such as the one or more programs 320, and provides scheduling, input-output control, file and data management, memory management, and communication control and related services. The operating system 314 may be, for example Windows NT, Windows 2000, Windows XP, Windows Vista, Windows 7, Windows 8, Windows 10, Windows Server 2003/2008 (all available from Microsoft, Corp. of Redmond, Wash.), Solaris (available from Sun Microsystems, Inc. of Palo Alto, Calif.), LINUX (or another UNIX variant) (available from Red Hat of Raleigh, N.C. and various other vendors), Android and variants thereof (available from Google, Inc. of Mountain View, Calif.), Apple OS X and variants thereof (available from Apple, Inc. of Cupertino, Calif.), or the like.

The one or more programs 320 may include a virtual machine engine 151 (FIG. 4A), an artificial intelligence module 152 (FIG. 4A), and a provider application 153 (FIG. 4A), and the programs 320 may be configured to implement the various processes, algorithms, methods, techniques, etc. described herein.

Figure 3:
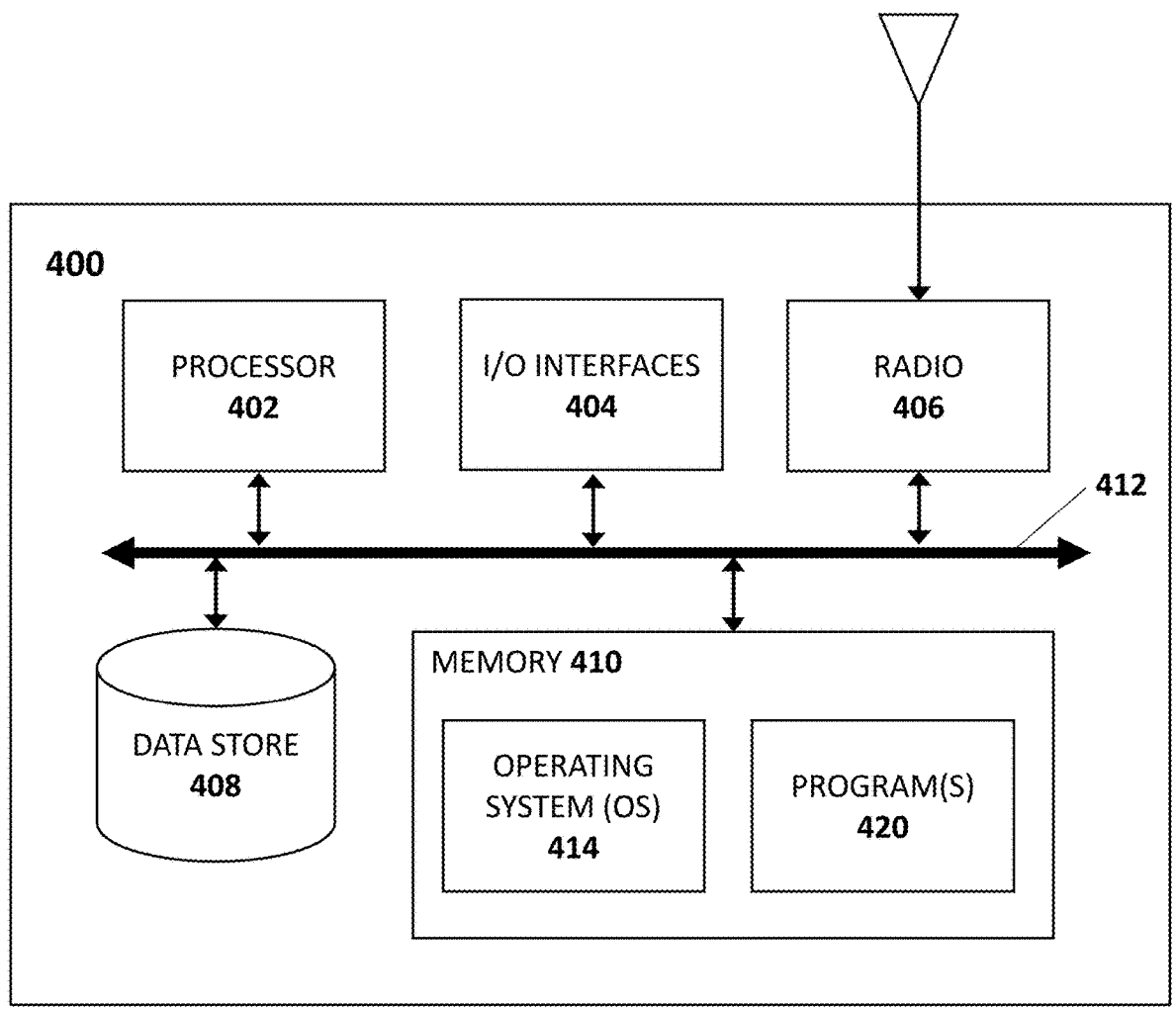
FIG. 3 shows a block diagram illustrating an example of a client device which may be used by the system as described in various embodiments herein.

Referring to FIG. 3, in an exemplary embodiment, a block diagram illustrates a client device 400 of which one or more may be used in the system 100 or the like and which may be a type of computing platform. The client device 400 is operable to be a digital device that, in terms of hardware architecture, generally includes a processor 402, input/output (I/O) interfaces 404, a radio 406, a data store 408, and memory 410. It should be appreciated by those of ordinary skill in the art that FIG. 3 depicts the client device 400 in an oversimplified manner, and a practical embodiment may include additional components and suitably configured processing logic to support known or conventional operating features that are not described in detail herein. The components (402, 404, 406, 408, and 410) are communicatively coupled via a local interface 412. The local interface 412 is operable to be, for example but not limited to, one or more buses or other wired or wireless connections, as is known in the art. The local interface 412 is operable to have additional elements, which are omitted for simplicity, such as controllers, buffers (caches), drivers, repeaters, and receivers, among many others, to enable communications. Further, the local interface 412 may include address, control, and/or data connections to enable appropriate communications among the aforementioned components.

The processor 402 is a hardware device for executing software instructions. The processor 402 is operable to be any custom made or commercially available processor, a central processing unit (CPU), an auxiliary processor among several processors associated with the client device 400, a semiconductor-based microprocessor (in the form of a microchip or chip set), or generally any device for executing software instructions. When the client device 400 is in operation, the processor 402 is configured to execute software stored within the memory 410, to communicate data to and from the memory 410, and to generally control operations of the client device 400 pursuant to the software instructions. In an exemplary embodiment, the processor 402 may include a mobile optimized processor such as optimized for power consumption and mobile applications.

The I/O interfaces 404 are able to be used to receive data and user input and/or for providing system output. User input is able to be provided via a plurality of I/O interfaces 404, such as a keypad, a touch screen, a camera, a microphone, a scroll ball, a scroll bar, buttons, bar code scanner, voice recognition, eye gesture, and the like. System output is able to be provided via a display screen 404A such as a liquid crystal display (LCD), touch screen, and the like. The I/O interfaces 404 are operable to also include, for example, a global positioning service (GPS) radio, a serial port, a parallel port, a small computer system interface (SCSI), an infrared (IR) interface, a radio frequency (RF) interface, a universal serial bus (USB) interface, and the like. The I/O interfaces 404 are operable to include a graphical user interface (GUI) that enables a user to interact with the client device 400. Additionally, the I/O interfaces 404 are operable to be used to output notifications to a user and are able to include a speaker or other sound emitting device configured to emit audio notifications, a vibrational device configured to vibrate, shake, or produce any other series of rapid and repeated movements to produce haptic notifications, and/or a light emitting diode (LED) or other light emitting element which may be configured to illuminate to provide a visual notification.

The radio 406 enables wireless communication to an external access device or network. Any number of suitable wireless data communication protocols, techniques, or methodologies are able to be supported by the radio 406, including, without limitation: RF; IrDA (infrared); Bluetooth; ZigBee (and other variants of the IEEE 802.15 protocol); IEEE 802.11 (any variation); IEEE 802.16 (WiMAX or any other variation); Direct Sequence Spread Spectrum; Frequency Hopping Spread Spectrum; Long Term Evolution (LTE); cellular/wireless/cordless telecommunication protocols (e.g. 3G/4G, etc.); wireless home network communication protocols; paging network protocols; magnetic induction; satellite data communication protocols; wireless hospital or healthcare facility network protocols such as those operating in the WMTS bands; GPRS; proprietary wireless data communication protocols such as variants of Wireless USB; and any other protocols for wireless communication.

The data store 408 may be used to store data and is therefore a type of memory. The data store 408 may include any of volatile memory elements (e.g., random access memory (RAM, such as DRAM, SRAM, SDRAM, and the like)), nonvolatile memory elements (e.g., ROM, hard drive, tape, CDROM, and the like), and combinations thereof. Moreover, the data store 408 may incorporate electronic, magnetic, optical, and/or other types of storage media.

The memory 410 may include any of volatile memory elements (e.g., random access memory (RAM, such as DRAM, SRAM, SDRAM, etc.)), nonvolatile memory elements (e.g., ROM, hard drive, etc.), and combinations thereof. Moreover, the memory 410 may incorporate electronic, magnetic, optical, and/or other types of storage media. Note that the memory 410 may have a distributed architecture, where various components are situated remotely from one another, but is able to be accessed by the processor 402. The software in memory 410 is operable to include one or more software programs 420, each of which includes an ordered listing of executable instructions for implementing logical functions. In the example of FIG. 3, the software in the memory system 410 includes a suitable operating system (O/S) 414 and programs 420.

The operating system 414 essentially controls the execution of other computer programs, and provides scheduling, input-output control, file and data management, memory management, and communication control and related services. The operating system 414 may be, for example, LINUX (or another UNIX variant), Android (available from Google), Symbian OS, Microsoft Windows CE, Microsoft Windows 7 Mobile, Microsoft Windows 10, iOS (available from Apple, Inc.), webOS (available from Hewlett Packard), Blackberry OS (Available from Research in Motion), and the like.

The programs 420 of a client device 400 may include a virtual machine engine 151 (FIG. 4A), a provider application 153 (FIG. 4A), a patient application 154 (FIG. 4A), and various applications, add-ons, etc. configured to provide end user functionality with the client device 400. For example, exemplary programs 420 may include, but not limited to, a web browser, social networking applications, streaming media applications, games, mapping and location applications, electronic mail applications, financial applications, and the like. In a typical example, the end user typically uses one or more of the programs 420 along with a network 105 to manipulate information of the system 100.

Figure 4A:
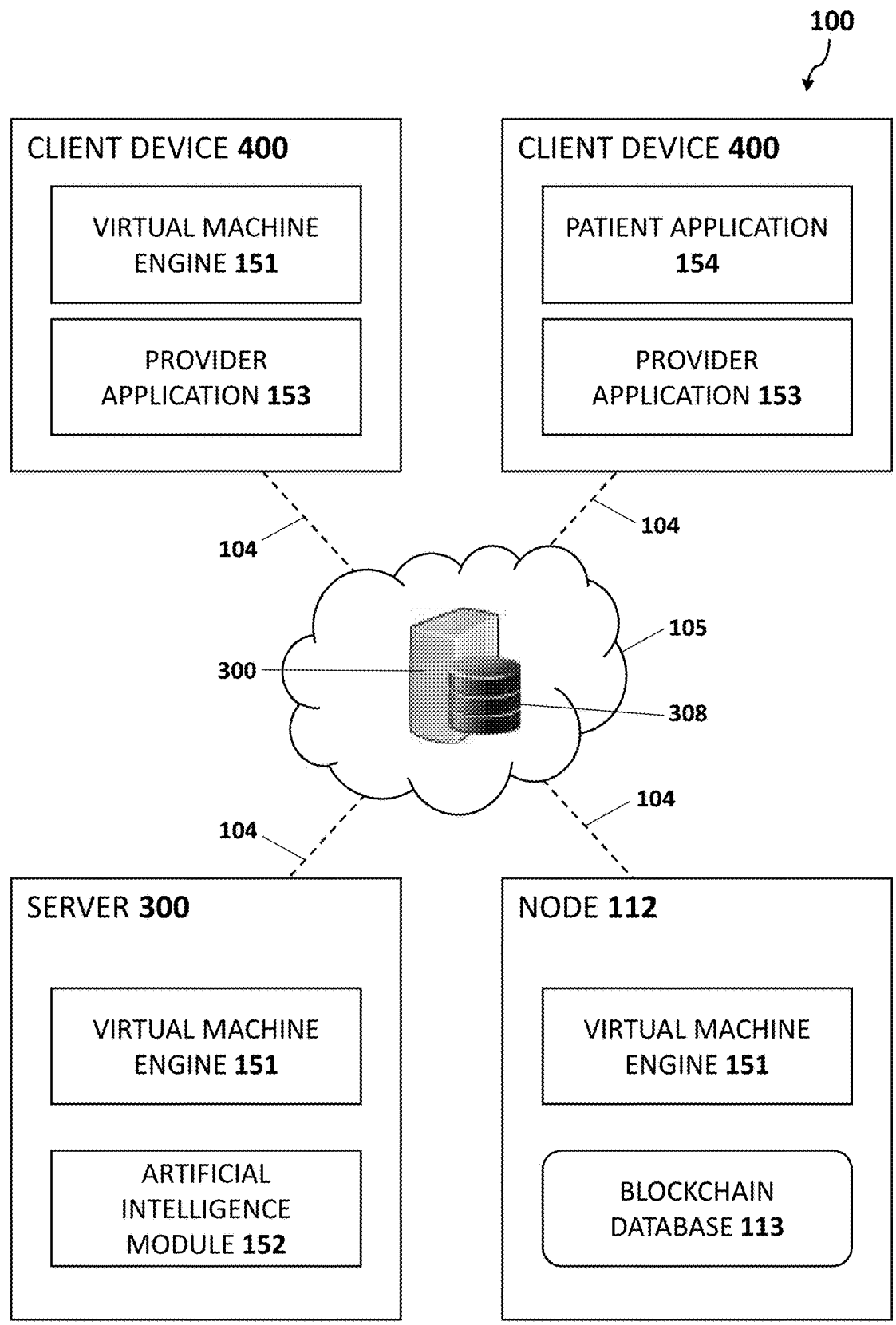
FIG. 4A depicts a block diagram illustrating some applications of a system for predicting the health and therapeutic behavior of individuals which may function as software rules engines according to various embodiments described herein.

Referring now to FIG. 4A, a block diagram showing some software rules engines and databases which may be found in a system 100 is illustrated. In some embodiments, the system 100 may comprise a virtual machine engine 151, an artificial intelligence module 152, a provider application 153, and/or a patient application 154. The engines 151, 152, 153, 154, may comprise one or more of the programs 320 of a server 300, and/or programs 420 of a client device 400 of the system 100. Preferably, the system 100 may comprise a blockchain network 111 comprising one or more nodes 112 in which one or more servers 300 and client devices 400 may function as or comprise one or more of the nodes 112. Each node 112 of the blockchain network 111 may maintain a blockchain database 113 which may comprise a distributed ledger of the blockchain network 111. One or more of the engines 151, 152, 153, 154, may read, write, or otherwise access data in the blockchain database(s) 113 of the system 100. Additionally, the engines 151, 152, 153, 154, may be in electronic communication so that data may be readily exchanged between the engines 151, 152, 153, 154. It should be understood that the functions attributed to the engines 151, 152, 153, 154, described herein are exemplary in nature, and that in alternative embodiments, any function attributed to any engine 151, 152, 153, 154, may be performed by one or more other engines 151, 152, 153, 154, or any other suitable processor logic.

A virtual machine engine 151 may comprise or function as virtual machine logic stored in memory 310, 410 which may be executable by the processor 302, 402, of one or more servers 300 and/or client devices 400 that may be functioning as a node 112. In some embodiments, the virtual machine engine 151 may manage and perform data transactions on the blockchain database 113 of a node 112, and the virtual machine engine 151 may be run by a processor 302, 402, of a node 112, to maintain a distributed ledger (copy of the blockchain database 113) on its memory 310, 410, and may thus synchronize transaction data with other nodes 112 containing the distributed ledger in order to implement a blockchain based transaction processing system 100. In further embodiments, a virtual machine engine 151 may provide access to data of the blockchain database 113 of a server 300 or client device 400.

As shown in FIG. 4B, the system 100 may comprise one or more blockchain databases 113 that may contain healthcare data, which may include healthcare data of one or more, and preferably a plurality of, patients 101B. A blockchain database 113 may comprise a distributed ledger in which a copy of the blockchain database 113 is stored and maintained by one or more nodes 112 of a blockchain network 111. In some embodiments, the data of a blockchain databases 113 may be maintained as a continuously growing ledger or listing of the data, which may be referred to as blocks, secured from tampering and revision. Each block includes a timestamp and a link to a previous block. Through the use of a peer-to-peer blockchain network 111 and a distributed timestamping server 300, a blockchain database 113 may be managed autonomously. Consensus ensures that the shared ledgers are exact copies, and lowers the risk of fraudulent transactions, because tampering would have to occur across many places at exactly the same time. Cryptographic hashes, such as the SHA256 computational algorithm, ensure that any alteration to transaction data input results in a different hash value being computed, which indicates potentially compromised transaction input. Digital signatures ensure that data entry transactions (data added to the blockchain database 1113) originated from senders (signed with private keys) and not imposters. At its core, a blockchain database 113 may record the chronological order of data entry transactions with all nodes 112 agreeing to the validity of entry transactions using the chosen consensus model. The result is data entry transactions that are irreversible and agreed to by all members in the blockchain network 111. In one embodiment, the blockchain network 111 is extended through the side chain, allowing not only currency transactions, but also legally binding contracts and certificates, audio files, and video files to be stored.

In some embodiments, a blockchain database 113 may store the healthcare data 120 of a plurality of patients 101B. Preferably, the healthcare data 120 of each patient 101B may be encrypted in the blockchain database 113. In further embodiments, the healthcare data 120 of a patient 101B may include one or more conditions 121, limiting factors 122, compliance records 123, therapeutic behavior patterns 124, successful therapies 125, unsuccessful therapies 126, possible therapies 127, probability of disease progression 128, predicted rate of disease progression, cost quotes 129, and successful probability thresholds 130. In one embodiment, healthcare data is operable to include age, gender, body composition, pregnancy status, organ function (e.g. heart, liver, kidneys), blood clotting issues, drug therapeutic index, prior pharmacokinetic and pharmacodynamic responses to previously and currently prescribed medications, pharmacogenetics, and pharmacogenomics. In still further embodiments, a blockchain database 113 may store one or more smart contracts 131 and cryptocurrency tokens 132 which may be associated with the healthcare data 120 of one or more patients 101B. Advantageously, patients control their own healthcare data 120 and all of the healthcare data 120 is in one unified location on the blockchain database 113. This is in contrast to the prior art, where the healthcare data 120 is owned by a multitude of organizations including hospitals and other health services providers, insurance companies, and government agencies. In one embodiment, a mobile and/or desktop application provides patients with direct access to their healthcare data and enables patients to share some, all, or none of their healthcare data with any specific physician or healthcare provider. In one embodiment, patients transfer a cryptographic token to provide access to their healthcare data on the blockchain database. In the prior art, the healthcare data 120 is also broken up; that is to say, results of a patient's last cardiovascular screening are not stored in the same place as the notes and prescription information from the same patient's last dermatology appointment, which are not stored in the same location as the same patient's family medical history and results from most recent routine physical. Congregating all healthcare data 120 and providing the individual with ownership of their own information decreases time related to future medical diagnoses and decision making, reduces administrative error, and decreases costs to the patient. As a whole, the present healthcare system manages patients' individual costs. The patient is operable to provide others with access to their unique healthcare data 120, such as insurance companies or healthcare providers, but receives the choice to do so. In one embodiment, the patient provides others with access to just a portion of their unique healthcare data, such as providing an orthodontist access to X-rays taken by a dentist, but to no other healthcare data. Healthcare data 120 is further operable to include, but is not limited to, consultation data, other medical history data, medical procedure data, claims data, eligibility data, prescription data, and outcomes data.

Furthermore, by aggregating all of a patient's healthcare data 120 in one location, the speed at which transactions are able to occur in the health network is increased. As this is expanded to all patients and all healthcare data, the speed at which a healthcare system is able to operate is increased dramatically, as patients, healthcare providers, insurance providers, and other members of the healthcare community do not have to wait for information or search for information, and the artificial intelligence system is able to make quicker recommendations due to having more information available. By placing all information in a common location on a distributed ledger, including treatment and medicine fees, transactions between parties such as patients and physicians, patients and insurers, physicians and insurers, patients and hospitals, hospitals and insurers, and any other relevant parties are more efficient and are also recorded and are therefore traceable. In one embodiment, all healthcare data 120 is available to physicians and other providers in an anonymized matter, providing more data for them to make informed decisions for the sake of their patients. In one embodiment, all healthcare data 120 is available to insurance companies and other financial providers in an anonymized matter, improving their ability to create better health plans as well as approve and fill claims in a more efficient manner. All healthcare data 120 stored on the distributed ledger is compliant with the Health Insurance Portability and Accountability Act (HIPAA) in order to protect patient privacy. The aggregation of the healthcare data 120 of all individuals, or in another embodiment selected groups of individuals, provides a larger training set for the artificial intelligence system to better understand the healthcare needs of every individual as well as larger communities. In another embodiment, the aggregation of the healthcare data 120 of all individuals, or selected groups of individuals, is used to negotiate improved rates with healthcare providers and insurance providers.

An artificial intelligence module 152 may comprise or function as artificial intelligence logic stored in memory 310, 410 which may be executable by the processor 302, 402, of one or more servers 300 and/or client devices 400. The artificial intelligence module 152 is located on top of the blockchain database. In some embodiments, the artificial intelligence module 152 may function as or comprise a machine/deep learning/artificial intelligence platform that interrogates the healthcare information or data of the system 100 and learns about healthcare behaviors and trends of one or more patients 101B. The artificial intelligence module 152 consistently undergoes algorithm testing and validation based on new healthcare data available. Data is operable to come from a variety of sources, which includes, but is not limited to, wearable data, clinical trials, clinical studies from physicians, scientists, healthcare clinics, physiotherapists, and radiologists. In further embodiments, the artificial intelligence module 152 may function to provide and recommend solutions, such as therapies which are cost effective and which may successfully treat a condition 121 of a patient 101B, to patients and healthcare providers 101A. In still further embodiments, the artificial intelligence module 152 may function to generate population data and other informatics, such as anonymized general patient population data, for healthcare organizations and pharmaceutical companies using information of one or more patients 101B stored in one or more data stores 308, 408, and/or blockchain databases 113. In one embodiment of the present invention, the artificial intelligence module 152 requires a means of verification of data. Senior clinicians verify that the data used for the learning algorithm of the artificial intelligence module 152 is correct in specificity, sensitivity, and relevance to the population and to comorbidities. The artificial intelligence module 152 is also governed by an algorithm which includes a set number of clinical rules, which identifies the correlation of drug/drug interactions. For example, the artificial intelligence module 152 is taught not to recommend one particular drug with another and why, and this draws on clinical data from one or more pharmaceutical companies and what is recorded in social media and other clinical papers. After data is verified, the algorithm of the artificial intelligence module 152 is run on the data and one or more rules are developed, as well as exception variants. The exception variants are reviewed by clinicians to examine for relevant efficacy. In one embodiment the exception variants are found to be clinically and scientifically relevant and become the new understanding of the artificial intelligence module 152. When reviewing new patient data.

A provider application 153 may comprise or function as provider logic stored in memory 310, 410 which may be executable by the processor 302, 402, of one or more servers 300 and/or client devices 400. In some embodiments, a provider application 153 may provide a user interface, such as a dashboard, that allows providers 101A and healthcare organizations to review patient 101B consented details and healthcare information. In further embodiments, a provider application 153 may function to provide or effect payment for healthcare services.

A patient application 154 may comprise or function as patient logic stored in memory 310, 410 which may be executable by the processor 302, 402, of one or more servers 300 and/or client devices 400. In some embodiments, a patient application 154 may provide a user interface, such as a portal, that allows patients 101B to review their medical needs in one convenient application to identify appropriate or successful therapies 125 and treatments. In further embodiments, a patient application 154 may provide a user interface that allows patients 101B to gain or access financial incentives through following or complying with treatments and therapies, improving their health, and sharing analyzed data with third party organizations as well as paying for drugs via cryptocurrency of the system 100 or other payment option. In still further embodiments, a patient application 154 may provide a user interface that allows a prescriber or other healthcare provider 101A to receive incentives, which may include cryptocurrency, other financial incentives, goods, services, or any other type of incentive, for working with the system 100 to keep a patient 101B on and following appropriate cost-effective therapies.

Figure 5:
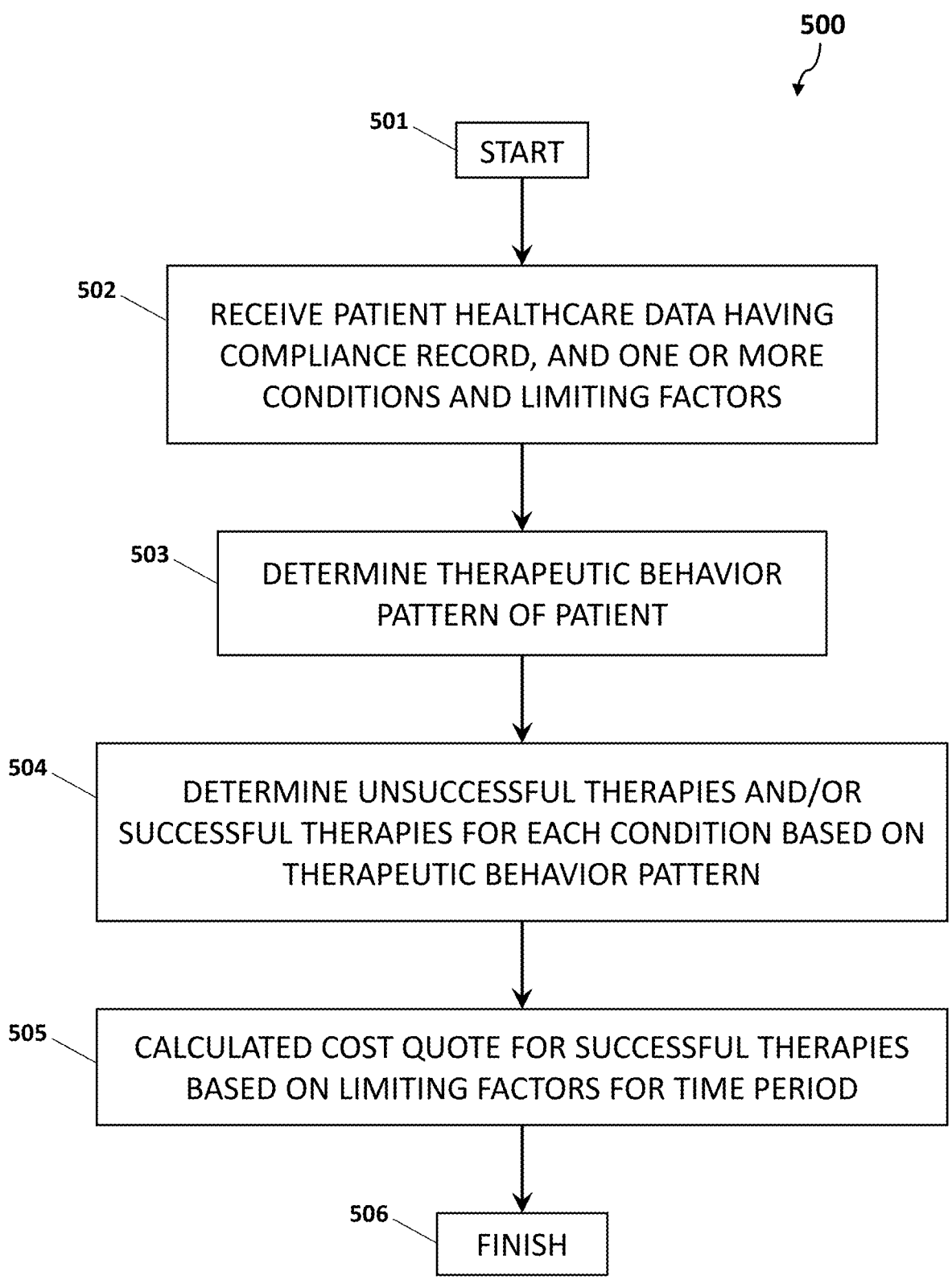
FIG. 5 illustrates a block diagram of an example of a computer-implemented method of predicting the health and therapeutic behavior of patients according to various embodiments described herein.

FIG. 5 shows a block diagram of an example of a computer-implemented method for predicting the health and therapeutic behavior of patients ("the method") 500 according to various embodiments described herein. In some embodiments, the method 500 may be used to predict changes in a patient 101B as well as provide information which may be used to predict a healthier lifestyle and/or disease remediation or slowing of disease progression for the patient 101B through changes in lifestyle circumstances, changes in drug types and information on interactions with other drugs that the patient 101B is taking. Furthermore, the method 500 may be used to predict drug usage for a patient 101B and to outline a drug usage and cost schedule for a period of time. One or more steps of the method 500 may be performed by a virtual machine engine 151, artificial intelligence module 152, provider application 153, and/or patient application 154 which may be executed by a computing device processor, such as a processor 302 (FIG. 2) and/or a processor 402 (FIG. 3).

The method 500 may start 501 and healthcare data of a patient 101B having a compliance record 123, one or more conditions 121 and limiting factors 122 may be received in step 502. In some embodiments, the healthcare data may be received by an artificial intelligence module 152 from the client device 400 of a provider 101A and/or patient 101B. In further embodiments, the healthcare data may be retrieved from the blockchain database 113 via a virtual machine engine 151 preferably of a client device 400. When a patient joins the healthcare system of the present invention, they authorize the sharing of their healthcare data to the blockchain database 113, and the artificial intelligence module 152 has, by default, access to all healthcare data stored on the blockchain database 113. Limiting factors 122 of a patient 101B may include existing drugs and therapies, lifestyle behaviors (such as smoking, weight changes, and mental health situations), if the patient 101B is ambulatory, or any other information which may limit the ability of the patient 101B to access or complete a therapy. Conditions 121 of a patient 101B may include any type of health condition 121, such as asthma, hypertension, hypercholesteremia, fragile X syndrome, depression, penicillin allergy, and any other condition 121 or disease state which may affect the health and wellbeing of the patient 101B. A compliance record 123 of a patient 101B may include data which describes the dosing schedule for one or more medications prescribed to the patient 101B along with the amount and timing of the refills for the one or more medications that the patient 101B has received. As an example, in step 502, the artificial intelligence module 152 may receive healthcare data of a patient 101B having an existing condition 121 of eczema, a new condition 121 of athletes' foot, a limiting factor 122 of bipolar disorder, and a compliance record 123 for the existing condition 121 that includes refill information on an oral prescription and a topical prescription for the existing condition 121 of eczema. In another embodiment, limiting factors 122 include activity level and ability to change activity level, dietary habits and ability to change dietary habits, stress including work-related stress, and any other factor which has the potential to impact a future therapy plan for a patient. In another embodiment, the compliance record 123 of a patient is operable to include factors such as attendance at appointments with physicians and other healthcare providers, adherence to medication, a history of taking medications not prescribed to the patient, a history of selling or trading medications illicitly, and any other factor which is likely to contribute to the overall success or the overall failure of future therapy plans.

In step 503, the therapeutic behavior pattern 124 of the patient 101B may be determined. In some embodiments, an artificial intelligence module 152 may use the healthcare information of the patient 101B to review the compliance record 123 of the patient 101B during one or more therapies to determine the therapeutic behavior pattern 124 of the patient 101B. For example, the artificial intelligence module 152 may review prescription refill information to determine if the patient 101B has a history of taking medications correctly or the artificial intelligence module 152 may review if a patient is following a dialysis schedule as directed. By determining the therapeutic behavior pattern 124 of the patient 101B, the artificial intelligence module 152 may determine how likely the patient 101B will be compliant with future therapies. Continuing the above example, a compliance record 123 for a patient 101B may include oral prescriptions and topically applied prescriptions for the existing condition 121 of eczema, with the patient 101B consistently refilling the topically applied prescriptions, but sporadically filling the oral prescriptions. In one embodiment, the artificial intelligence module 152 queries the patient as to the reasons why compliance is low, such as why compliance to oral medications is low. For example, compliance is operable to be low due to multiple daily doses (e.g. 3-4 times daily), prohibitive side effects, difficult dosing directions, cost of medications themselves, or adjunct medications provided to ameliorate side effects. The intelligence module 152 may determine that the therapeutic behavior pattern 124 of the patient 101B has a high probability of compliance for topically applied prescriptions and a low probability of compliance for oral prescriptions.

In step 504, one or more unsuccessful therapies 126 and/or successful therapies 125 for each condition 121 may be determined by the artificial intelligence module 152 based on the therapeutic behavior pattern 124 of step 503. Therapies 125, 126, may include: procedures, such as laboratory tests; medical devices and digital health technologies; prescriptive drugs, such as prescription drugs, compounded drugs, veterinary prescription drugs, specialty pharmacy medications, medical *cannabis*; phytocannabinoids; terpenoid molecules; other compounds; or any other therapy which may be used to treat a condition 121 for that patient 101B. In some embodiments, after assessment of a current disease state status, the artificial intelligence module 152 may aggregate a review of medications and therapies that have been tried and failed (or those of similar mechanism of action and/or potency) as well as the current medications being taken. From this evaluation the artificial intelligence module 152 may compute and determine precluded or unsuccessful therapies 126 (those that wouldn't be prescribed) and possible successful therapies 125, including pharmacotherapeutic considerations, for that patient 101B. Continuing the above example, the artificial intelligence module 152 may determine that a first therapy of a first topical prescription for the new condition 121 of athletes' foot would not interfere with the patient's 101B current topical prescription for eczema and based on the therapeutic behavior pattern 124 of the patient 101B having a high probability of compliance for topically applied prescriptions, the artificial intelligence module 152 may determine that the first therapy of a first topical prescription for the new condition 121 of athletes' foot would be a successful therapy 125 which may be used to treat the new condition 121. As another example, the artificial intelligence module 152 may determine that a second therapy of a second oral prescription for the new condition 121 of athletes' foot would interfere with the patient's 101B current topical prescription for eczema and based on the therapeutic behavior pattern 124 of the patient 101B having a low probability of compliance for oral prescriptions, the artificial intelligence module 152 may determine that the second oral prescription for the new condition 121 of athletes' foot would be an unsuccessful therapy 126 which may not be used to treat the new condition 121.

In further embodiments, one or more unsuccessful therapies 126 and/or successful therapies 125 for each condition 121 may be determined by the artificial intelligence module 152 based on the one or more limiting factors 122 of step 502. Optionally, after assessment of a current disease state status, the artificial intelligence module 152 may aggregate a review of the one or more limiting factors 122 of the patient 101B. From this evaluation the artificial intelligence module 152 may compute and determine precluded or unsuccessful therapies 126 (those that wouldn't be prescribed) and possible successful therapies 125, including pharmacotherapeutic considerations, for that patient 101B. Continuing the above example, the artificial intelligence module 152 may determine that a third therapy of a third topical prescription for the new condition 121 of athletes' foot would not interfere with the patient's 101B current topical prescription for eczema and that the limiting factor 122 of bipolar disorder has little to no impact on the typical patients' ability to take the third topical prescription as prescribed. The artificial intelligence module 152 may then determine that the third therapy of a third topical prescription for the new condition 121 of athletes' foot would be a successful therapy 125 which may be used to treat the new condition 121. As a further example, the artificial intelligence module 152 may determine that a fourth therapy of a fourth topical prescription for the new condition 121 of athletes' foot would not interfere with the patient's 101B current topical prescription for eczema and that the limiting factor 122 of bipolar disorder has a significant impact on the typical patients' ability to take the third topical prescription as prescribed due to it having a possible side effect of exacerbating bipolar symptoms. The artificial intelligence module 152 may then determine that the fourth therapy of a fourth topical prescription for the new condition 121 of athletes' foot would be an unsuccessful therapy 126 which may not be used to treat the new condition 121.

In step 505, a cost quote 129 for the successful therapies 125 determined in step 504 may be calculated based on the limiting factors 122 for a desired time period. In some embodiments, the artificial intelligence module 152 may calculate the cost of each therapy which may be used to successfully treat a condition 121 of the patient 101B. The cost calculation may include weighting the limiting factors 122 of the patient 101B. For example, a patient 101B that has a limiting factor 122 of a poor record of attending checkups and doctor visits or being noncompliant may add a twenty percent increase to the cost of a therapy which requires frequent patient checkups and monitoring. In one embodiment, the artificial intelligence module 152 queries the patient as to the reason for the limiting factor such as noncompliance. Additionally, the cost calculation may include the cost of providing the therapy to the patient 101B for a desired or specified time period, such as six months or a year. In this manner, a cost quote 129 may be provided by the artificial intelligence module 152 for each possible therapy 127 which may be used to treat a patient 101B for a condition 121. The cost quote 129 may be saved in the healthcare information of the patient 101B stored in the blockchain database 113 which may be made available to the patient 101B via a patient application 154 and to one or more providers 101A via a provider application 153. In preferred embodiments, the fixed fee quote may be made available to payers so that a determination is able to be made to institute fixed-fee schedule. After step 505, the method 500 may finish 506.

Figure 6:
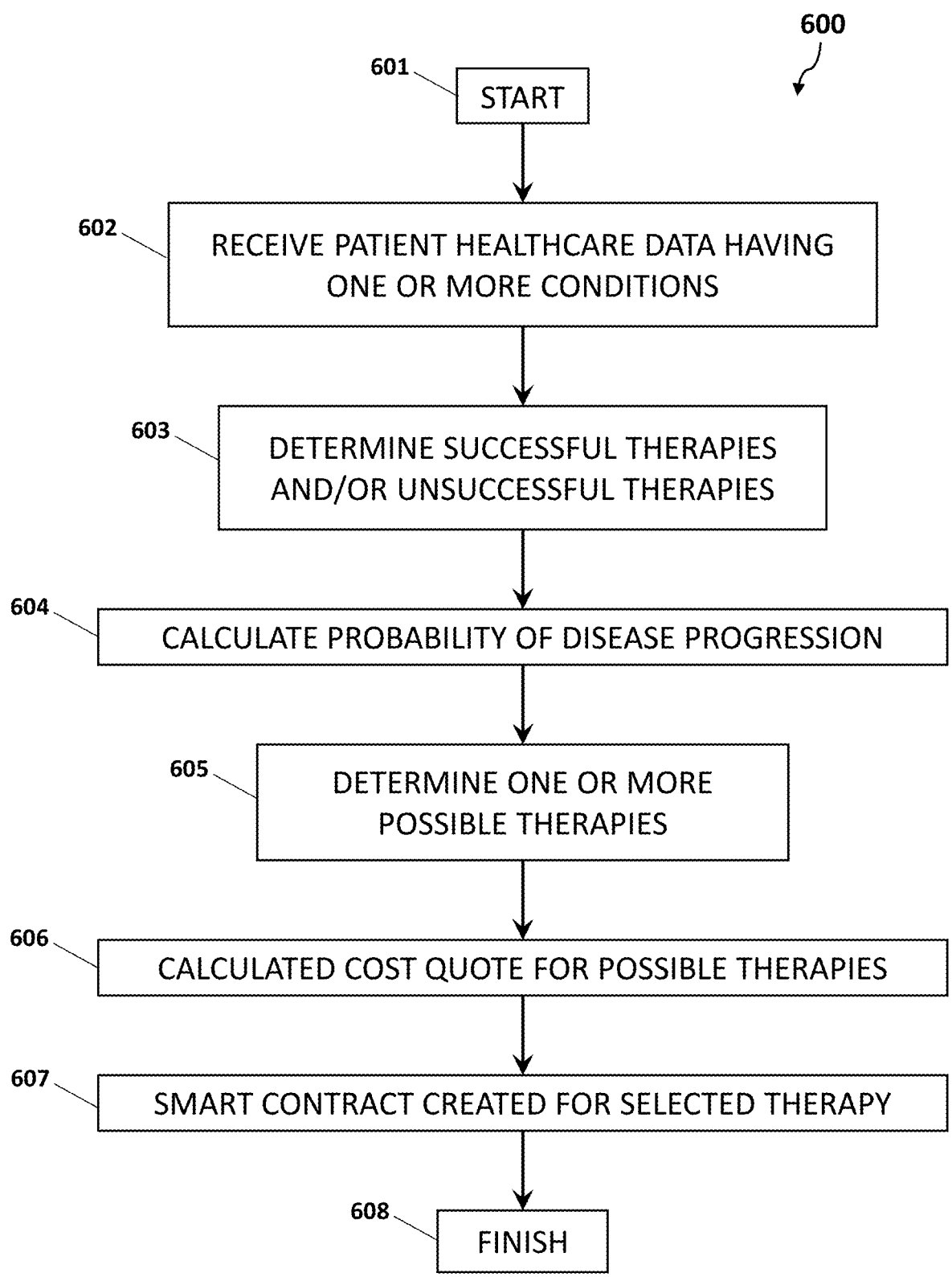
FIG. 6 shows a block diagram of an example of a computer-implemented method of providing cost effective therapy for a patient according to various embodiments described herein.

FIG. 6 depicts a block diagram of an example of a computer-implemented method of providing cost effective therapy for a patient ("the method") 600 according to various embodiments described herein. In some embodiments, the method 600 may be used to predict the cost of providing a therapy to a patient 101B to treat a condition 121 of the patient 101B in which the patient has one or more other conditions 121 that the patient 101B may be being treated for. One or more steps of the method 600 may be performed by a virtual machine engine 151, artificial intelligence module 152, provider application 153, and/or patient application 154 which may be executed by a computing device processor, such as a processor 302 (FIG. 2) and/or a processor 402 (FIG. 3).

The method 600 may start 601 and healthcare data for a patient 101B may be received in step 602. In preferred embodiments, the healthcare data for a patient 101B received in step 602 may include one or more new conditions 121 for the patient 101B. In some embodiments, the healthcare data may be received by an artificial intelligence module 152 from the client device 400 of a provider 101A and/or patient 101B. In further embodiments, the healthcare data may be retrieved from the blockchain database 113 via a virtual machine engine 151 preferably of a client device 400. The patient 101B, provider 101A, and/or payer may provide healthcare data to the system 100 which may include drug data, such as the National Drug Code (NDC) for drugs prescribed in the United States which are approved by the Food and Drug Administration, primary coding, secondary coding (preferably via International Classification of Diseases, Tenth Revision, Clinical Modification (ICD-10-CM) coding for disease states), co-morbidities, genomics, lifestyle choices, laboratory values, a compliance record 123, one or more conditions 121 and limiting factors 122 which may be stored in a blockchain database 113. Every drug can be categorized based on its mechanism of pharmacologic activity, and there may be drugs with many different mechanisms of action used to treat the same disease state. In further embodiments, the healthcare data may be retrieved from the blockchain database 113 via a virtual machine engine 151. Limiting factors 122 of a patient 101B may include existing drugs and therapies, lifestyle behaviors (such as smoking, weight changes, and mental health situations), if the patient 101B is ambulatory, or any other information which may limit the ability of the patient 101B to access or complete a therapy. In step 603 one or more successful therapies 125 and/or unsuccessful therapies 126 may be determined for the one or more new conditions 121 for the patient 101B. Preferably, the artificial intelligence module 152 may determine one or more therapeutic categories along with the unsuccessful therapies 126 and successful therapies 125. In some embodiments, the artificial intelligence module 152 may assess the current disease state status of a condition 121 of the patient 101B, and the artificial intelligence module 152 may aggregate a review of therapies, such as medications, that have been tried and failed (or those of similar mechanism of action and/or potency) as well as the current medications being taken by the patient 101B. From this evaluation the artificial intelligence module 152 may compute and determine precluded or unsuccessful therapies 126 (those that wouldn't be prescribed) and possible successful therapies 125, including pharmacotherapeutic considerations, for that patient 101B. Therapies 125, 126, may include: procedures, such as laboratory tests; medical devices and digital health technologies; prescriptive drugs, such as prescription drugs, compounded drugs, veterinary prescription drugs, specialty pharmacy medications, medical *cannabis*; phytocannabinoids; terpenoid molecules; other compounds; vaccines and monoclonal antibodies; or any other therapy which may be used to treat a condition 121 for that patient 101B. In further embodiments, all possible therapeutic and pharmacologic combinations of therapies may be examined and determined to be pharmacologically and therapeutically appropriate. In still further embodiments, therapies may be included or precluded based on cost, comorbidities, drug-drug interactions, drug-disease interactions, drug-laboratory interactions, genomic considerations, and pharmacogenetic and pharmacogenomic considerations. In considering various drugs, each drug category is essentially a silo where all of the agents in that particular silo have the same mechanism of action. The main differences between each drug include the potency of the drug, side effect profile, and how many times a day it is necessary to give the drug to have the desired effect. There are many rules based on acquired-knowledge that are put in place to prevent harm, for example, only one drug per pharmacologic category is ever used at a time to treat a patient. As another example, certain categories of medications work well with each other while other categories added together are not only unbeneficial but are in fact harmful to the patient. Nationally recognized guidelines clearly define drugs that are preferred to treat patients with specific demographics and co-morbidities. As in the case of cancer and NCCN guidelines the list of agents is altered from FDA-approved to also include those agents used as "off-label" which have a substantive level of evidence of their safety and efficacy in a particular disease as determined by past research efforts.

In step 604, the probability of disease progression 128 of a new condition 121 of the patient 101B may be calculated. In some embodiments, the artificial intelligence module 152 may perform the calculation for each condition 121 of the patient 101B. For example, the patient 101B may have a primary condition 121, secondary condition 121, tertiary condition 121 of any other number of conditions 121. The artificial intelligence module 152 may determine the unknown variable of the likelihood of disease progression, resolution or stability that queries the categories indicated, that would be indicated, or potentially indicated, but not contraindicated, to treat a primary condition 121 based upon the healthcare information of the blockchain database 113, such as historical therapies that may include prescriptive drugs and/or phytocannabinoids and/or terpenoid compounds or medications taken, the current prescription drugs and/or phytocannabinoid and/or terpenoid compounds or medications taken and the patient's response to them, as well as to the mechanism of action and the potential prescription drugs and/or phytocannabinoid and/or terpenoid agents used for the primary condition 121 to control the primary condition 121, as the response is as expected, above expected or below expected, therefore the condition 121 may maintain, progress or recede. Historical therapies may also include: procedures, such as laboratory tests; medical devices and digital health technologies; prescriptive drugs, such as prescription drugs, compounded drugs, veterinary prescription drugs, specialty pharmacy medications, medical *cannabis*; phytocannabinoids; terpenoid molecules; other compounds; or Then the secondary condition 121 or limiting factor 122 if present may preclude some prescriptive and/or phytocannabinoid and/or terpenoid agents, categories based on that condition 121 and the likelihood of progression or resolution based upon the global objective and/or subjective assessment of the condition 121 of the patient 101B over the fixed time period under consideration. The process and its inherent complexity increases with each condition 121 and/or limiting factor 122 presented and may be repeated for a tertiary condition 121 and any other number of conditions 121.

In step 605, one or more possible therapies 127 for a new condition 121 may be determined by the artificial intelligence module 152. Possible therapies 127 may include: procedures such as laboratory tests, medical devices and digital health technologies, prescriptive drugs such as prescription drugs, compounded drugs, 3-D printed drugs, veterinary prescription drugs, specialty pharmacy medications, medical *cannabis*, phytocannabinoids, terpenoid molecules, other compounds, surgeries, physical therapies, vitamins, nootropics, medical foods such as foods to improve cognitive function, vaccines, immunotherapies, monoclonal antibodies, or any other therapy which may be used to treat a condition 121 of a patient 101B. The artificial intelligence module 152 may use the successful therapies 125 determined in step 603 as the possible therapies 127 which may be used to treat the new condition 121. Possible therapies 127 may include prescriptive drugs, phytocannabinoids, terpenoid agents, or any other treatment which may be used to treat the condition 121. In preferred embodiments, the possible therapies 127 may be ranked by probability of successful treatment of a new condition 121 of the patient 101B, such as the primary condition 121, may be determined by the artificial intelligence module 152. Preferably, all possible therapies 127 may be determined and may be assigned ranking for successful treatment. The artificial intelligence module 152 may rank the possible therapies 127 based on the likelihood of the therapy successfully treating the condition 121. This likelihood may be based on the compliance record 123 and one or more conditions 121 and limiting factors 122 of the patient 101B. As an example, an artificial intelligence module 152 may determine two possible therapies 127, such as a first therapy and a second therapy, and the artificial intelligence module 152 may rank the first and second possible therapies 127 by probability of the first and second possible therapies 127 being a successful treatment, wherein the probability of success is based on factors including patient compliance, the patient's existing condition or existing conditions, treatment cost, and historical success rate of the treatments as determined from information stored on the blockchain database. As a further example, the artificial intelligence module 152 may rank the second possible therapy 127 (an oral phytocannabinoid) higher than the first possible therapy 127 (a topical prescription) since the patient has a higher compliance record 123 with oral therapies than they do with topical therapies.

Defining disease states by way of the ICD-10-CM code gives the ability to determine all of the FDA-approved drugs for that condition. These drugs can be identified by NDC number and arranged categorically by pharmacologic action. Once the disease and drugs are identified and labeled numerically by ICD and NDC nomenclature, they are arranges preferentially based on recognized guidelines and consensus publications. By identifying the drugs which the patient is currently taking, they system is able to eliminate a large number of similar medications that the patient will not receive due to the accumulated knowledge of drug scheduling, actions, and potencies.

In step 606, a cost quote 129 for the possible therapies 127 is calculated. Preferably, a fixed quote may be provided for each possible therapy 127 using ICD-10 coding and the NDC code for all drug therapies required to successfully and therapeutically treat the patient 101B for fixed period of time may be calculated by the artificial intelligence module 152. In some embodiments, artificial intelligence module 152 may calculate the cost quote 129 for one or more therapies which exceed a successful probability threshold 130. For example, the artificial intelligence module 152 may calculate the cost quote 129 for all therapies having a probability of successfully treating the condition 121 that is greater than seventy fiver percent. The artificial intelligence module 152 may determine the overall function and economics of a fixed period of time with an unknown variable of the likelihood of disease progression. One or more categories of therapies, such as prescription drugs and/or phytocannabinoids and/or terpenoid could be used with or in place of the current prescriptive drugs and/or phytocannabinoid and/or terpenoid regimen considering the best and worst-case scenarios to generate a list of candidate prescriptive drugs and/or cannabinoid and/or terpenoid molecules or compounds relative to the economics, preferably over a fixed period of time. The categories of therapies may also include: procedures such as laboratory tests, medical devices, and digital health technologies, prescriptive drugs such as prescription drugs, compounded drugs, 3-D printed drugs, veterinary prescription drugs, specialty pharmacy medications, and medical *cannabis*, phytocannabinoids, terpenoid molecules, vitamins, nootropics, medical foods such as foods to improve cognitive function, vaccines, immunotherapies, monoclonal antibodies, or any other therapy which may be used to treat a condition 121 of a patient 101B. These cost quotes 129 and possible therapies 127 may be provided to a patient 101B via a patient application 154 and to a provider 101A via a provider application 153. In some embodiments, each patient subject variable set may be weighted as to the likelihood of occurrence to calculate the potential need for prescriptive and/or phytocannabinoid and/or terpenoid drug change which results impact the cost variable. Patient 101B categories may be disease based, prescriptive and/or phytocannabinoid and/or terpenoid drug based and are operable to be utilized to impact patient contribution or co-payment to affect disease control and improved outcome. In this manner overall cost of the prescriptive and/or phytocannabinoid and/or terpenoid therapeutic regimen is operable to be better managed yet individual patient participation on all levels are able to be controlled.

In step 607, a smart contract 131 may be created for a selected therapy. A smart contract 131 is a computer protocol intended to digitally facilitate, verify, or enforce the negotiation or performance of a contract. Smart contracts 131 allow the performance of credible transactions without third parties. These transactions are trackable and irreversible. In some embodiments, a patient 101B and/or provider 101A may select a desired therapy that was returned in step 606. The therapy may be provided to the patient 101B and a record of the provision of the therapy may be stored in the blockchain database 113 of the virtual machine engine 151. This record may be used by the virtual machine engine 151 to generate a smart contract 131 associated with the selected therapy provided to the patient 101B which may be stored in a database, such as the blockchain database 113. The virtual machine engine 151 may use data from this contract and one or more client devices 400 to fulfill the terms of the smart contract 131 which may provide compensation to the patient 101B and the one or more providers 101A associated with providing the selected therapy to the patient 101B. In preferred embodiments, a smart contract 131 may be paid for all therapies related to a single ICD-10 code for an agreed upon fixed period of time. In some embodiments, a fixed-fee payment may be received prospectively which would reduce administrative costs for the payer and enable better control of patient by managing adherence, compliance and persistence. Upon completion of step 607, the method 600 may finish 608.

Smart contracts 131 also provide a mechanism to track the reliability of patients, physicians, pharmacies, hospitals, insurance companies, and other service providers over time, as well as provide increased levels of transparency for all parties involved. Smart contracts 131 also provide another level of information to the artificial intelligence system, including, but not limited to types of medications prescribed, who has fulfilled prescriptions, who has written prescriptions, and who has picked up their prescriptions. All of these factors impact future treatment plan recommendations. For example, in one embodiment, if a patient has a history of not picking up a filled prescription, as indicated by the smart contract 131 which is stored on the distributed ledger, the artificial intelligence system is more likely to include lifestyle changes in a treatment plan as an alternative to a medication which the patient is not likely to be compliant with taking. In another embodiment, based on the smart contracts 131 stored on the distributed ledger, it is seen that an insurance company takes a longer time to reimburse patients, and as such, the artificial intelligence system is more likely to recommend patients register with another insurance company. The smart contract further ensures compliance between two individuals or organizations in relation to what they have agreed, such as between a physician and a patient, wherein the patient is rewarded if their health is improved.

Figure 7A:
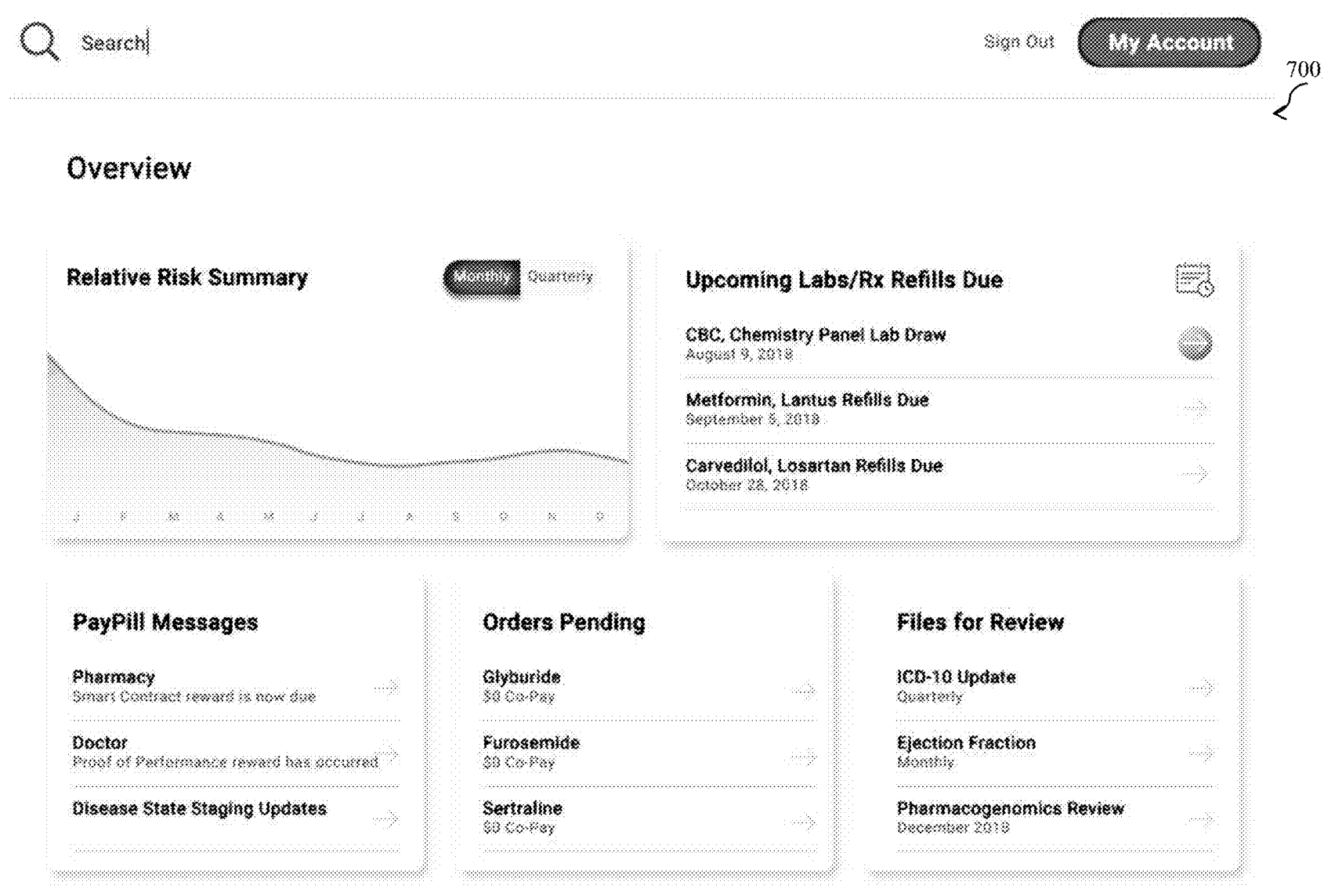
Figure 7B:
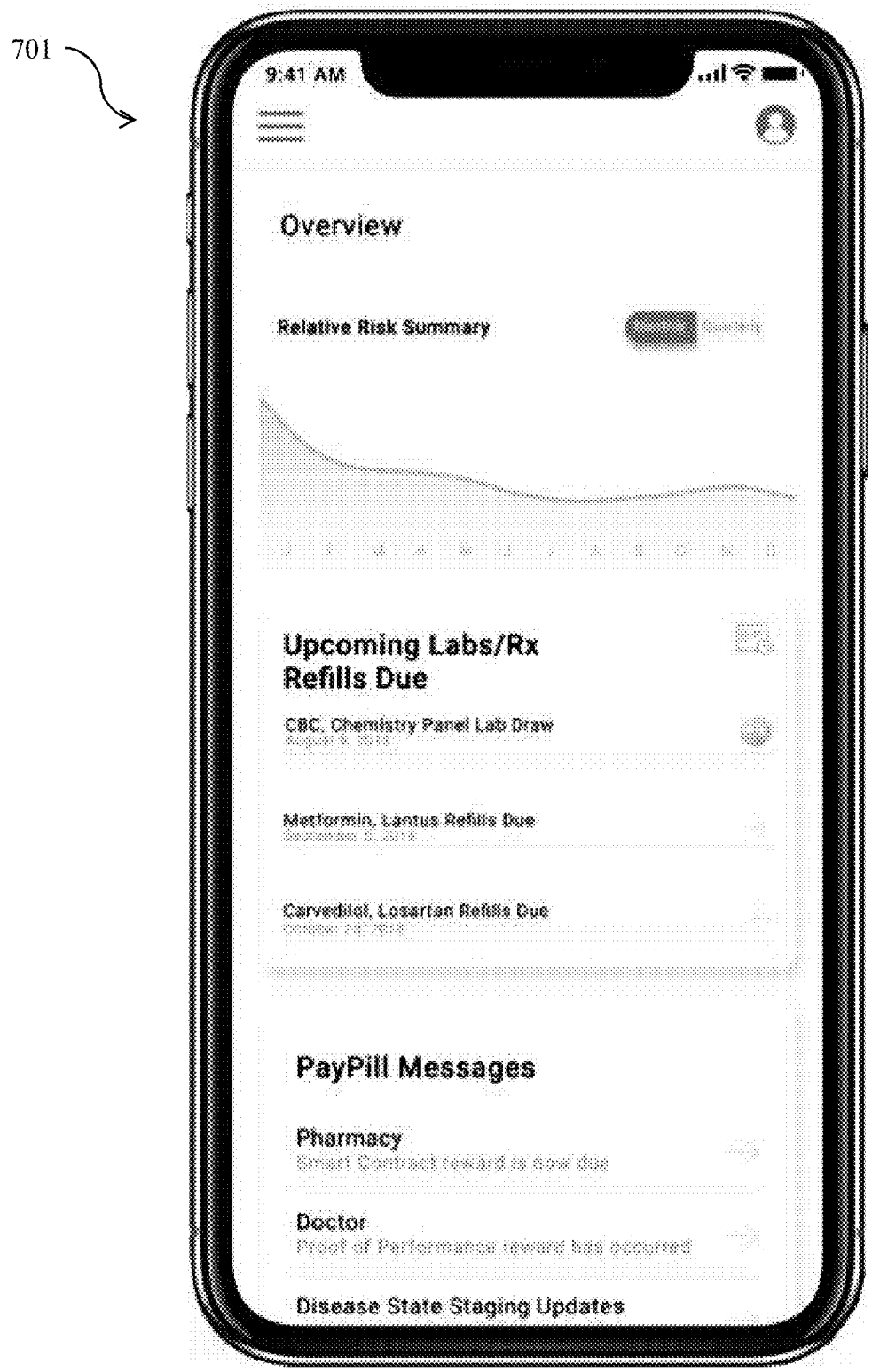
FIG. 7B illustrates a patient dashboard on a mobile application providing access to all health information, according to one embodiment of the present invention.

FIG. 7A illustrates a patient dashboard 700 providing access to all health information for the patient. Because all of a patient's data is aggregated in one location on the distributed ledger, the patient dashboard 700 allows the patient to view all of their data. The patient dashboard 700 allows patients to review healthcare information from all relevant healthcare institutions, including, but not limited to, hospitals, physicians, insurance providers, pharmacies, research labs, federal agencies, and any other relevant service provider. The patient dashboard 700 further allows patients to access alternative healthcare solutions unique to their needs, which are generated by the artificial intelligence system. In one embodiment of the present invention, the patient's unique treatment plans, generated by the artificial intelligence system, are available to be viewed, inspected, and selected on the patient dashboard 700. In another embodiment of the present invention, patients use the patient dashboard 700 to complete health related activities, including placing prescription dispensing and refill requests with pharmacies, scheduling appointments, initiating smart contracts, receiving payments from insurance companies and other organizations, making payments to insurance companies, pharmacies, hospitals, physicians, and other organizations, and communicating directly with medical providers. In one embodiment of the present invention, the patient dashboard 700 illustrates at least, but is not limited to, upcoming labs and/or tests, upcoming refills due, messages such as from physicians, pharmacies, and hospitals, pending orders such as prescription orders, files to be reviewed by the patient, and a patient risk summary. The dashboard 700 is further operable to include a visual representation of the meaning of a patient's lab results, a measure of patient compliance, refill status, refill compliance, current smart contracts, and patient progress on individual smart contracts. A patient is able to access the patient dashboard 700 from any device which is able to connect to the internet, including, but not limited to, desktop computers, laptop computers, smart phones, personal digital assistants, and tablets. FIG. 7B illustrates an alternative embodiment of a patient dashboard 701 on a mobile application, which provides the patient with the same features and access to their health information as the patient dashboard 700 of FIG. 7A, including, but not limited to upcoming labs and/or tests, upcoming refills due, messages such as from physicians, pharmacies, and hospitals, pending orders such as for prescriptions, files to be reviewed by the patient, and a patient risk summary. The dashboard 701 on a mobile application is operable to utilize location-based services on the mobile device. In one embodiment, the dashboard 701 on a mobile application displays inventory management tools, delivery status, refill status, and smart contract reminders such as data provision, refills, in-person appointments and exams, and scheduled telepharmacy calls.

In one embodiment of the present invention, the artificial intelligence system develops a plan for a patient which is prescribed in part based on comorbidities. In one embodiment, the system takes into account comorbidities of the patient, which are operable to be one or more of diabetes, hypertension or high blood pressure, congestive heart failure (CHF), chronic obstructive pulmonary disease (COPD), cancers including leukemias carcinomas, sarcomas, melanomas, lymphomas or any other cancer, solid tumor, or liquid tumor including all hematological malignancies, chronic kidney disease (CKD), nephritis, nephrosis, cardiovascular diseases including, but not limited to, heart rhythm disorders, valvular diseases, coronary heart disease, or stroke, hyperlipidemia, pulmonary circulation disorders, peripheral vascular disorders, renal disease or failure, overweight or obesity, neurological disorders and conditions such as depression, anxiety, attention deficit disorder (ADD), attention deficit hyperactivity disorder (ADHD), bipolar disorder, panic disorder, eating disorders, schizophrenia, autism spectrum disorder, Alzheimer's disease, and personality disorders, paralysis, hypothyroidism, hyperthyroidism, liver disease, HIV/AIDS, rheumatoid arthritis, osteoarthritis, anemia, alcohol abuse, drug abuse, solid tumor(s), fluid and electrolyte disorders, epilepsy, nonalcoholic fatty liver disease, sleep apnea, gastrointestinal disturbances, pneumonia, pulmonary embolism, skin conditions such as athlete's foot, eczema, acne, shingles, hives, sunburn, contact dermatitis, rosacea, psoriasis, cellulitis, and measles, asthma, hypocholesteremia, hypercholesteremia, fragile X syndrome, allergies such as penicillin allergy, influenza A, influenza B, injuries or conditions wherein a steroid is prescribed, sexually transmitted diseases and infections including chlamydia, syphilis, gonorrhea, *Mycoplasma genitalium*, trichomoniasis, Human Papilloma Virus (HPV), and herpes, urinary tract infection, food poisoning, hepatitis A, hepatitis B, hepatitis C, staph bacteria, COVID-19, addiction and addiction management, dermatological conditions, fertility conditions, endocrinological conditions, gastrointestinal disease and Chron's disease, Immune Globulin deficiencies, multiple sclerosis, ophthalmological conditions, chronic pain management, rheumatological conditions, respiratory syncytial virus, transplantation, urological conditions, and any other disease or condition which is operable to be medicated, treated, or managed. Comorbidities and any other conditions experienced by the patient are operable to cause or require one or more other limiting factors including drugs, therapies, or lifestyle behaviors prescribed to limit or reduce the effects of the comorbidities or other conditions.

Comorbidities and their associated medications and treatment plans, as well as any other medications and treatment plans, are important in determining new medications and treatment plans which a patient is to be prescribed. In one embodiment of the present invention, prescriptions are compared to avoid known adverse side effects as well as dosage rates which provide positive and negative effects. For example, if a patient is already taking medication A for a preexisting condition, adding medication B to treat a secondary condition is operable to make the patient sicker or cause the patient to have an adverse reaction due to the effects of mixing medication A and medication B. In another example, if a patient is already taking medication A for a preexisting condition, adding a small dose of medication B to treat a secondary condition is operable to improve the patient's health, while adding a larger dose of medication B to treat a secondary condition is operable to negatively impact the patient's health. All medication and treatment plan information are anonymously stored on the distributed ledger in order to provide a larger database of medication and treatment plan information to further train the artificial intelligence system in future decision making. For example, in one embodiment, it is previously unknown that medication C and medication D, when taken together, cause adverse side effects. Because all medication and treatment information are stored on the distributed ledger, a physician and the artificial intelligence system will be aware of these side effects, and will not prescribe medication C and medication D together again for any other patient. The artificial intelligence algorithm is responsible for recommending the drug therapy for a patient, but a physician is responsible for prescribing the drug therapy. All final decision making is left up to the physician. A method of dispensing a prescription is operable to include: storing the prescription transaction in the distributed ledger, a plurality of pharmacies submitting providing submissions for dispensing the prescription, wherein the submissions are stored on the ledger, receiving indication of the pharmacy selected by the patient, recording the selection of the pharmacy by the patient on the distributed ledger, including a smart contract, with the submission including price and incentive for selection of the pharmacy, and once complete, the system recording on the ledger that the pharmacy dispensed the prescription.

The process of a pharmacy being selected and filling a prescription is further stored on a distributed ledger for increased data collection and transparency, which aids in minimizing costs to patients, improves decision making, and provides increased patient information security. In one embodiment, the method of locating a convenient pharmacy, such as a hospital pharmacy or neighborhood pharmacy, to dispense the selected prescription and have the selected prescription filled includes a generated prescription which has been signed by a physician being stored in a distributed ledger, one or more pharmacies providing a submission for dispensing the prescription by way of the distributed ledger, wherein the submissions are stored on the distributed ledger, and wherein the submissions include the price of the prescription, such as the cost per month or dose, and any incentives for selection of the pharmacy, such as rewards points or a cryptocurrency bonus. The patient then selects the pharmacy with which to fulfill the prescription based on this information, this decision is stored on the distributed ledger, and a smart contract is generated by the artificial intelligence system for the fulfillment of the prescription. Once the prescription has been dispensed by the pharmacy and obtained by the patient, it is recorded on the distributed ledger that the patient has received the prescription and associated information, such as time, date, and payment method. In one embodiment, pharmacies and other medical providers receive a trust score or a verification which is used by the artificial intelligence system to make healthcare recommendations.

In making recommendations for treatment plants, including, but not limited to, types of medications, physicians to consult with, hospitals to visit, pharmacies to fulfill prescriptions, and any other healthcare recommendations that comprise a treatment plan, the artificial intelligent system constantly takes into account and completes data analytics on new information on the distributed ledger. This data analysis leads to recommendations for treatment plans to include factors such as projected benefits, projected spending, and projected savings which are relayed to the patient or representative of the patient in order to make informed medical decisions. In one embodiment, the artificial intelligent system is also operable to calculate a probability of disease progression for the new condition based on receiving or not receiving therapy. In another embodiment, the artificial intelligence system is operable to calculate a probability of disease progression for one or more existing conditions based on receiving or not receiving therapy.

Over time, the present invention decreases costs in other aspects of the healthcare system as well. As healthcare data about a patient is aggregated over time, less and less new information is needed in order to generate treatment plans. Some tests will always be useful, such as taking a patient's temperature; however, some tests or labs at a hospital will not need to always be completed for a patient for at least two reasons. First, depending on if a patient has had the lab or test completed in the past, depending on the lab or test, it will not need to be run again because the results will be easily accessible by way of the distributed ledger and the aggregated patient healthcare data. Second, because of the aggregation of all patient data, more detailed analysis will be performed by the artificial intelligence system and more accurate recommendations will be made with less information. This is in part due to data analytics and the ability of the artificial intelligence system to update constantly any time new information is added to the distributed ledger. The improved recommendations of the artificial intelligence system will eliminate the need for some labs tests to be performed, specifically in the hospital setting, decreasing the time required to make treatment plan recommendations and decreasing costs to patients. The need for specific tests or data is preprogrammed into the system and all data collected is timestamped on the blockchain database.

In a preferred embodiment of the present invention, a cryptocurrency or digital asset is used as the medium of exchange for data and payment for goods and services, and is therefore required for any transfer of assets. In one embodiment, the cryptocurrency or digital asset includes a token. In one embodiment, the tokens serve as a reward or incentive to nodes for blockchain network services to make the blockchain network attack resistant. Tokens are operable to include usage tokens, work tokens, intrinsic, native, or built-in tokens, application tokens, asset-backed tokens, or any other type of token operable to be used in a cryptocurrency network. The blockchain network also utilizes token governance rulesets based on crypto-economic incentive mechanisms that determine under which circumstances blockchain network transactions are validated and new blocks are created. In the facilitation of the transfer of assets, the cryptocurrency or digital asset is operable to be used by patients, individuals or organizations acting on the behalf of patients, physicians, hospitals, insurance companies, other healthcare providers, and anyone else involved in the healthcare system. For example, the cryptocurrency or digital asset is operable to be used in, but not limited to, the purchase of medications or treatments, the payment for medical services, offset of the cost of medications or treatments, the refund of medications or treatments, the purchase of medical technologies, co-insurance payments or reimbursements, providing of incentives to individuals or organizations, access to anonymized medical information, access to one's own health information, access to another's health information, conversion to other currency types, transferred to others including family to assist in payment of their healthcare costs, rewarding of medical practices, reward of medical practices to be passed onto low or no income patients, pro rata share of value or income from sale or licensing of data to outside entities to be shared with patients who have allowed their data to be shared, or for any other asset transfer within the healthcare system. In one embodiment, the value of the cryptocurrency or digital asset varies based on the amount of medical information which has been placed on the distributed ledger, which encourages individuals to join the present system and to place all of their relative health information on the distributed ledger, as well as for pharmacies, hospitals, physicians, and other medical providers to encourage the use of the present system.

In another embodiment of the present invention, a cryptocurrency or digital asset is used to provide incentives. Individuals are able to receive payment in the form of cryptocurrency or digital assets for activities such as, but not limited to, as taking actions to improve their health, making their anonymized healthcare data to others, such as for research purposes, choosing specific drugs or healthcare services, and reducing their present and future healthcare costs if there is a demonstratable impact on their health.

In one embodiment of the present invention, a patient has a condition such as diabetes which provides a limiting factor of their medication, such as metformin, DPP-4 inhibitors, and/or insulin. As is common with diabetic individuals, the patient also has a comorbidity, such as hypertension, which requires further medical treatment, such as taking a diuretic or beta-blocker. The artificial intelligence system of the present invention is operable to first determine the therapeutic behavior pattern of the patient, and then, considering all known hypertension medications and treatment options, as well as any other conditions and limiting factors of the patient, determine unsuccessful therapies and/or successful therapies for diabetes and hypertension based on the therapeutic behavior pattern. By way of example, the artificial intelligence system recommends a specific hypertension medication based on known interactions between that medication and other medications which the patient is currently taking in order to maximize positive results for the patient. The artificial intelligence system is then operable to calculate a cost quote for the successful therapies based on limiting factors for a set time period, such as a weekly, monthly, quarterly, biannual, annual or biennial cost, and then generate a smart contract on a distributed ledger for a therapy selected by the patient and/or a medical professional chosen by the patient, such as a primary care physician. In one embodiment, the patient pays for the medication, once dispensed, via a cryptocurrency payment system. The cryptocurrency utilized is cryptocurrency issued by the system of the present invention. In one embodiment, the method of locating a pharmacy to dispense the selected prescription and having the prescription filled includes a generated prescription being stored in a distributed ledger, one or more pharmacies providing a submission for dispensing the prescription by way of the distributed ledger, wherein the submissions are stored on the distributed ledger, and wherein the submissions include the price of the prescription, such as the cost per month, and any incentives for selection of the pharmacy. The patient then selects the pharmacy with which to fulfill the prescription, this decision is stored on the distributed ledger, and a smart contract is generated for the fulfillment of the prescription. Once the prescription has been dispensed and obtained by the patient, it is recorded on the distributed ledger that the patient has retrieved the prescription and associated information, such as time, date, and payment method.

In another embodiment of the present invention, a patient with a condition such as Type 2 Diabetes requests information to regulate naturally their Type 2 Diabetes. The patient is current prescribed a series of oral medications to control their condition and is interested in learning if regulating their condition can be done naturally, resulting in a reduction or even an elimination of their drug dosages. The patient makes this request on the patient dashboard on a mobile application, and the artificial intelligence module calculates and attributes a percentage of the patient's overall response to each drug in the regimen in the form of response to objective or subjective markers demonstrating efficacy. The artificial intelligence module then takes data from research, other individuals, the user's health records and environmental activity and recommends a series of solutions. Upon receiving the recommended solutions, the patient discusses the solutions with their doctor and sets goals to monitor progress based on the solutions generated. This information is added to the patient's healthcare record and therefore the blockchain database. If the health outcomes for the patient are successful, the data involved in that success, such as, but not limited to, the change in drug dosing or scheduling, change in drug regiments, blood test, weight, and dietetics plan, is used to anticipate similar questions from other individuals. The individual is rewarded with cryptocurrency tokens for reducing the drug bill and therefore affecting the individual's healthcare insurance policy with a reduced cost policy. In another embodiment, the physician is also rewarded with cryptocurrency tokens for reducing the drug bill and therefore affecting the individual's healthcare insurance policy with a reduced cost policy.

In another embodiment of the present invention, a patient has a condition such as COPD which provides a limiting factor of their medication, such as a bronchodilator and/or steroid. As is common for individuals with COPD, the patient also has a comorbidity, such as peripheral artery disease, which requires further medical treatment, such as taking antiplatelet or anticlotting agents. The artificial intelligence system of the present invention is operable to first determine the therapeutic behavior pattern of the patient, and then, considering all known hypertension medications and treatment options, as well as any other conditions and limiting factors of the patient, determine unsuccessful therapies and/or successful therapies for COPD and peripheral artery disease based on the therapeutic behavior pattern. By way of example, the artificial intelligence system recommends a specific peripheral artery disease medication based on known interactions between that medication and other medications which the patient is currently taking in order to maximize positive results for the patient. The artificial intelligence system is then operable to calculate a cost quote for the successful therapies based on limiting factors for a set time period, such as daily, weekly, monthly, quarterly, biannual, annual, or biennial cost, and then generate a smart contract on a distributed ledger for a therapy selected by the patient and/or a medical professional chosen by the patient, such as a primary care physician. In one embodiment, the patient pays for the medication, once dispensed, via a cryptocurrency payment system as opposed to a traditional financial method such as by using a cash payment or with a credit or debit card.

In yet another embodiment of the present invention, a patient has a condition such as CHF which provides a limiting factor of their medication, such as an Angiotensin-converting enzyme (ACE) inhibitor or beta-blockers. As is common with diabetic individuals, the patient also has a comorbidity, such as renal insufficiency, which requires further medical treatment, such as dialysis or anti-hypertensives. The artificial intelligence system of the present invention is operable to first determine the therapeutic behavior pattern of the patient, and then, considering all known renal insufficiency medications and treatment options, as well as any other conditions and limiting factors of the patient, determine unsuccessful therapies and/or successful therapies for CHF and renal insufficiency based on the therapeutic behavior pattern. By way of example, the artificial intelligence system recommends a specific renal insufficiency medication based on known interactions between that medication and other medications which the patient is currently taking in order to maximize positive results for the patient. The artificial intelligence system is then operable to calculate a cost quote for the successful therapies based on limiting factors for a set time period, such as monthly, weekly, daily, quarterly, biannual, annual, or biennial cost, and then generate a smart contract on a distributed ledger for the therapy plan selected by the patient and/or a medical professional chosen by the patient, such as a primary care physician. In one embodiment, the patient pays for the medication, once dispensed, via a cryptocurrency payment system as opposed to a traditional financial method such as by using a cash payment or with a credit or debit card.

In yet another embodiment of the present invention, a patient has a condition such as chronic kidney disease which provides a limiting factor of their medication, such as diuretics, Erythropoietin, and/or dialysis. As is common for individuals with chronic kidney disease, the patient also has a comorbidity, such as hyperlipidemia, which requires further medical treatment, such as a statin or cholesterol medical like atorvastatin. The artificial intelligence system of the present invention is operable to first determine the therapeutic behavior pattern of the patient, and then, considering all known hyperlipidemia medications and treatment options, as well as any other conditions and limiting factors of the patient, determine unsuccessful therapies and/or successful therapies for chronic kidney disease and hyperlipidemia based on the therapeutic behavior pattern. By way of example, the artificial intelligence system recommends a specific hyperlipidemia medication based on known interactions between that medication and other medications which the patient is currently taking in order to maximize positive results for the patient. The artificial intelligence system is then operable to calculate a cost quote for the successful therapies based on limiting factors for a set time period, such as monthly cost, and then generate a smart contract on a distributed ledger for a therapy selected by the patient and/or a medical professional chosen by the patient, such as a primary care physician. In one embodiment, the patient pays for the medication, once dispensed, via a cryptocurrency payment system.

Figure 8A:
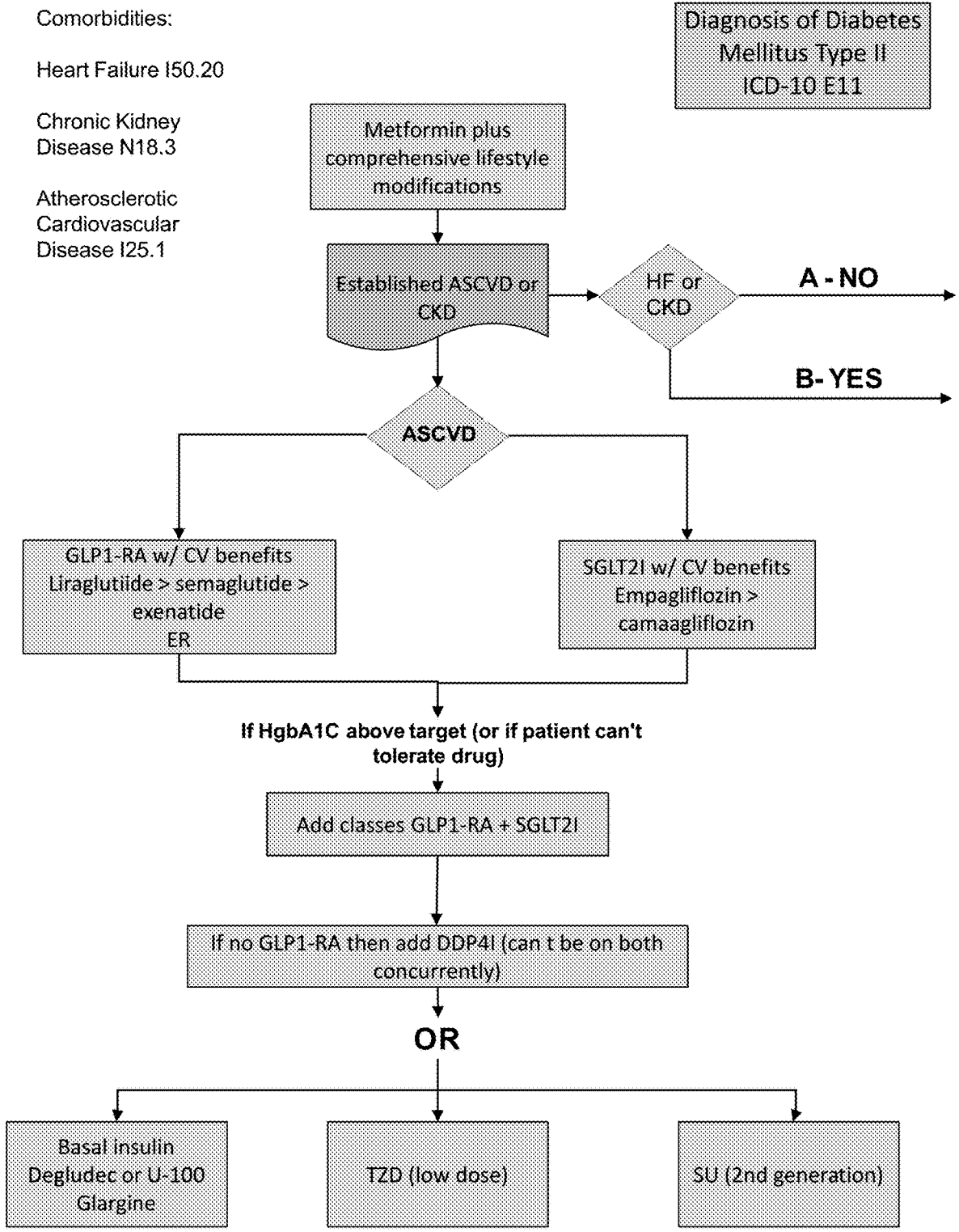
FIG. 8A illustrates a block diagram of a system for determining a drug therapy for a patient, according to one embodiment of the present invention.
Figure 8B:
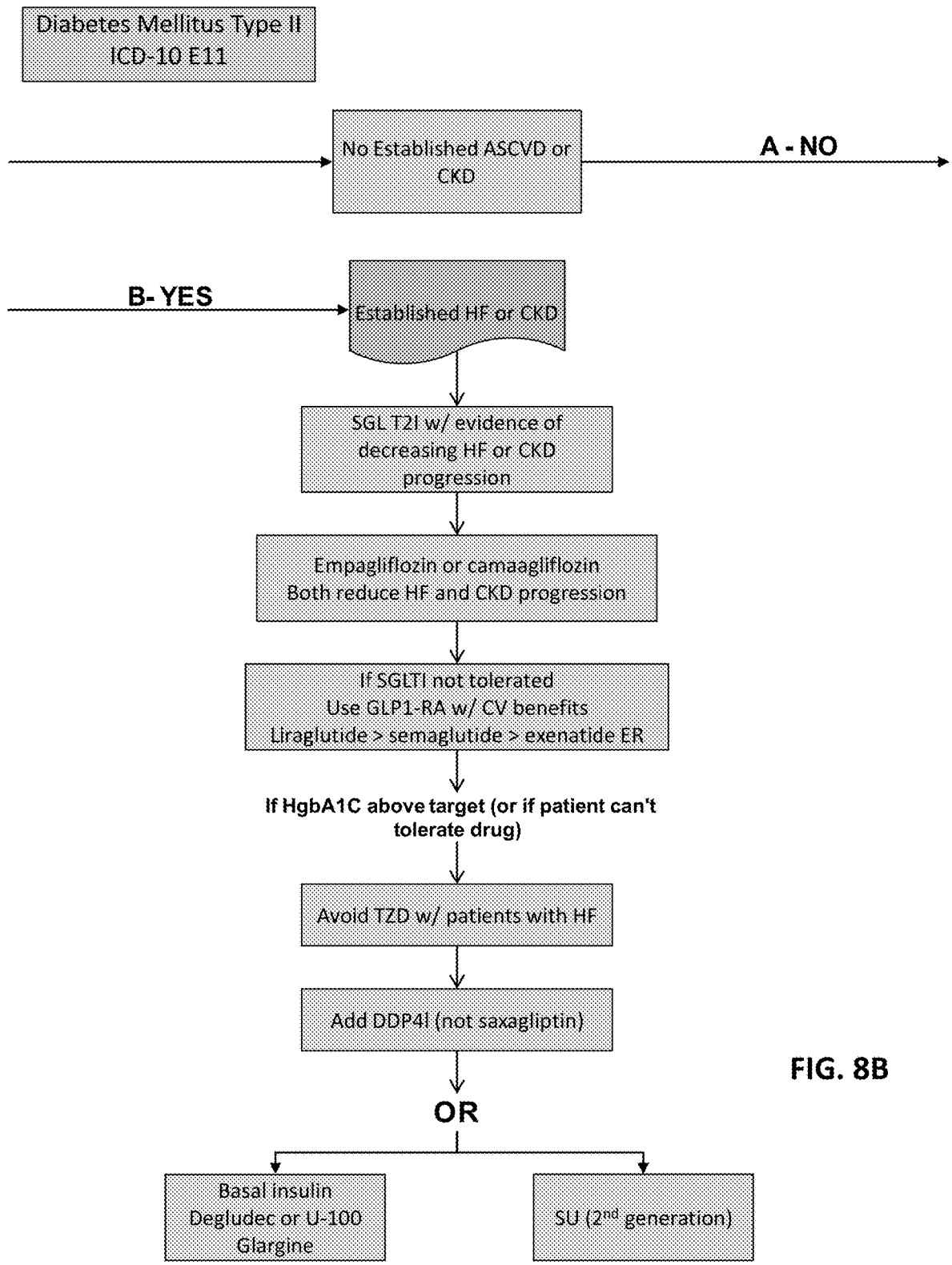
FIG. 8B illustrates a continuation of the block diagram of FIG. 8A of a system for determining a drug therapy for a patient, according to one embodiment of the present invention.
Figure 8C:
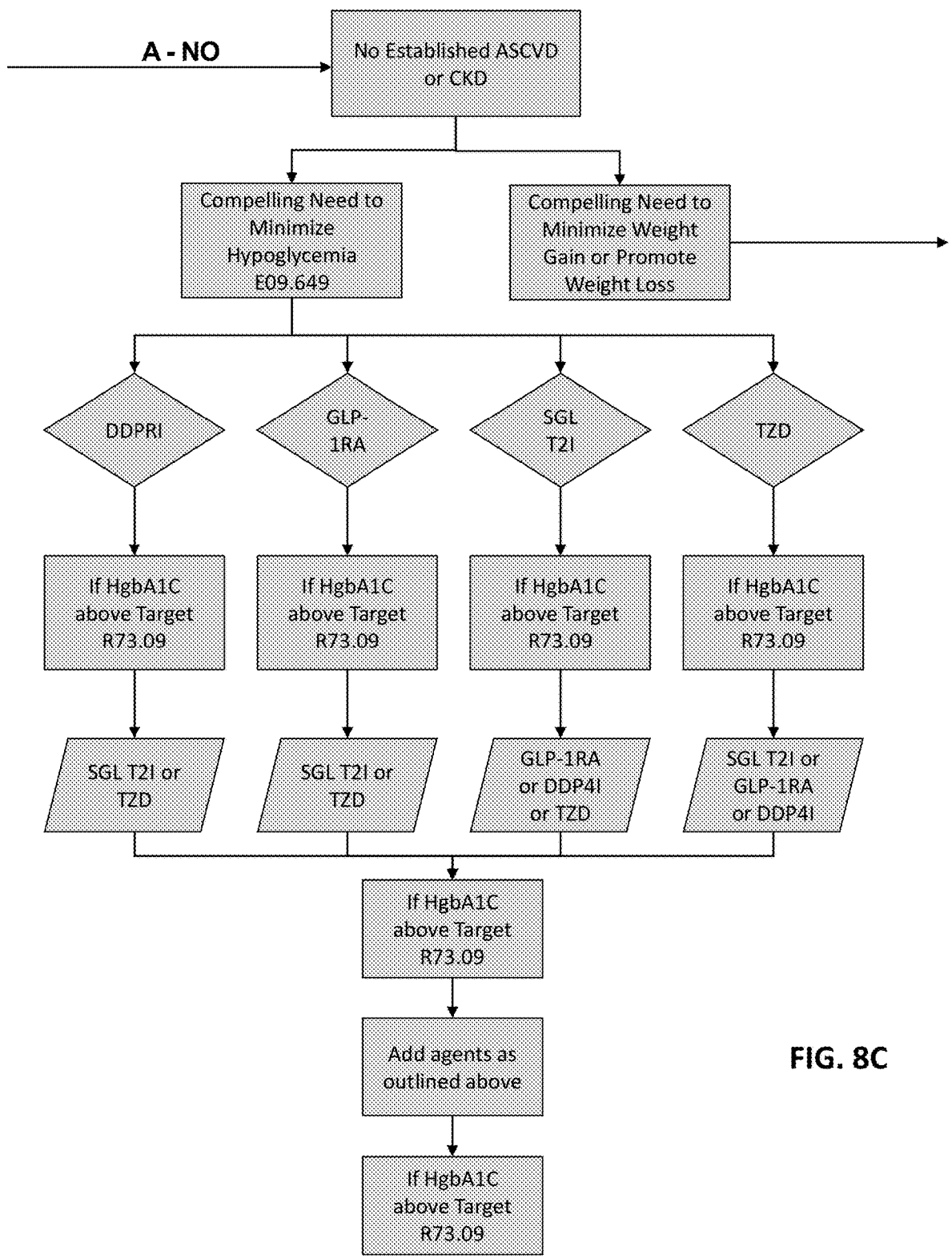
FIG. 8C illustrates a continuation of the block diagrams of FIG. 8A and FIG. 8B of a system for determining a drug therapy for a patient, according to one embodiment of the present invention.
Figure 9:
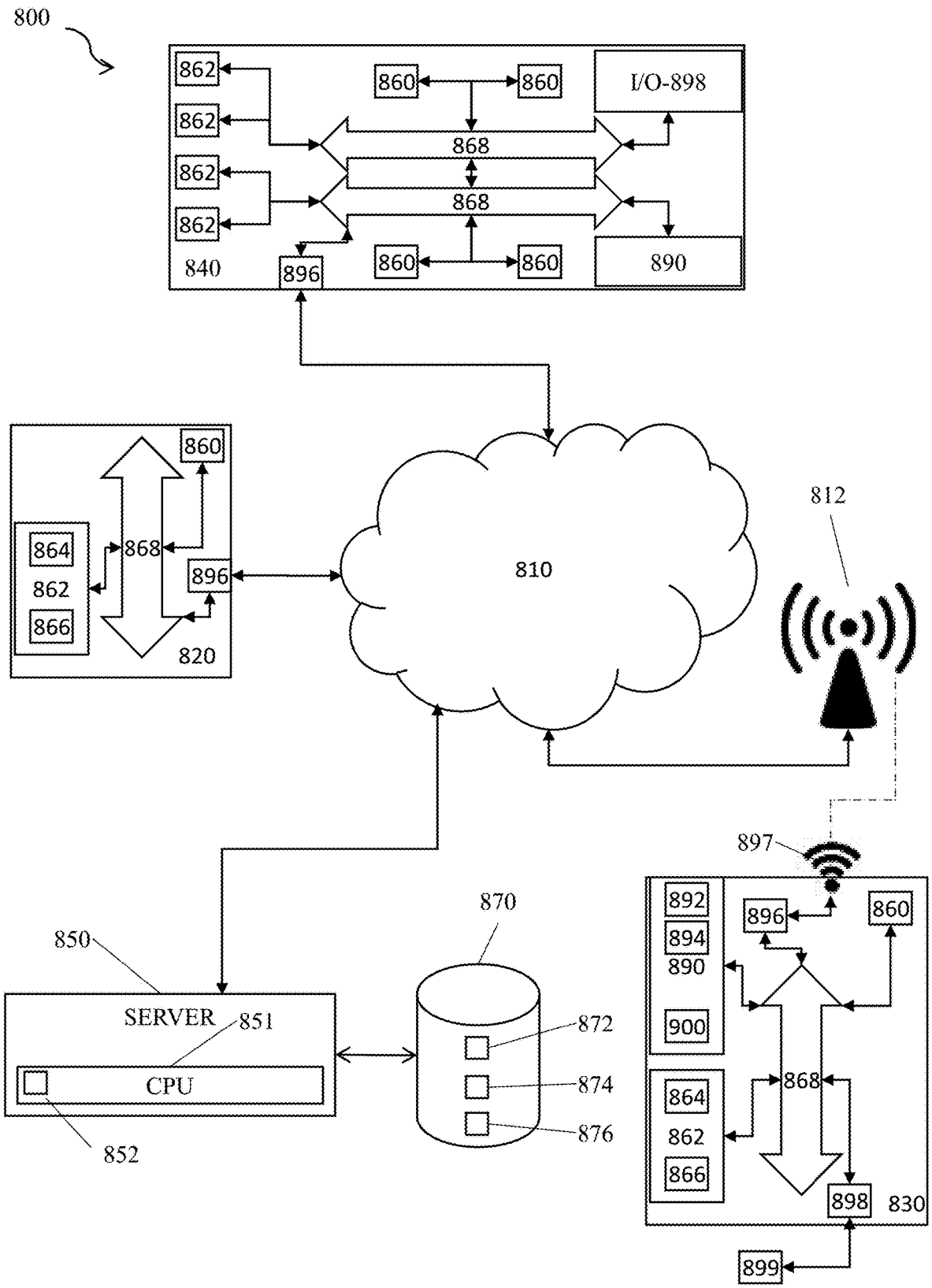
FIG. 9 is a schematic diagram of a system of the present invention.

In yet another embodiment of the present invention, a patient has a condition such as hypertension, or high blood pressure, and has a secondary diagnosis of Diabetes Mellitus Type II. FIGS. 8A, 8B, and 8C illustrate a block diagram of an algorithm for determining a drug treatment for a patient with this condition, however, it is understood that a similar process is operable to be used to other conditions. Hypertension often needs to be treated with several different types of drugs. There are 15 different pharmacologic classes of agents for use in the treatment of hypertension and within the class of agents there are subclasses based on the site of pharmacologic activity, mechanism/site of action and chemical structure. In the treatment of uncomplicated hypertension, thiazide-type diuretics are typically used as initial drug therapy, either alone or combined with drugs from other classes. In patients for whom diuretics are contraindicated or poorly tolerated, use of an ACE inhibitor, angiotensin receptor blocker, or calcium channel blocker is appropriate. Certain high-risk co-morbidities are compelling indications for the initial use of other antihypertensive drug classes. A compelling indication is an additional co-morbidity with corresponding ICD-10 CM coding associated with hypertension for which there is clinical trial evidence of a specific outcome benefit of a given class of antihypertensive drugs in both disease states. By way of example, the use of angiotensin-converting enzyme inhibitors or angiotensin receptor blockers is common in hypertensive patients with certain co-morbidities. Both of these categories of agents lower peripheral vascular resistance and blood pressure without reflex stimulation of heart rate and contractility. They reduce morbidity and mortality in patients with congestive heart failure, reduce systolic function in patients that are post-myocardial infarction, and retard progression of diabetic renal disease and hypertensive nephrosclerosis in chronic renal failure. In hypertensive patients with osteoporosis the use of thiazide diuretics is operable to preserve bone density and raise serum calcium levels. In certain other co-morbid conditions, the use of one or more particular categories of antihypertensive agents is sable to be related to potential deleterious effects and would be contraindicated in treating hypertension with this particular co-morbidity. Loop diuretics are associated with decreased serum calcium levels and are to be avoided in hypertensive patients with osteoporosis. Drugs chronically administered to patients with rheumatoid arthritis, such as NSAIDS, cyclo-oxygenase-2 (COX-2) inhibitors, oral corticosteroids, and some disease-modifying antirheumatic drugs (DMARDS) are operable to raise systolic and diastolic blood pressure levels by way of their individual mechanism of pharmacologic action. NSAIDS inhibit prostaglandin-mediated vasodilation and promote salt and water retention. Both of these mechanisms may contribute to NSAIDs partially reversing the effects of anti-hypertensive drugs, particularly those agents whose mechanism depends on modulating prostaglandins, renin, or sodium and fluid balance. Antihypertensive drugs appear to be affected to variable degrees by NSAIDs. Diuretics, angiotensin-converting enzyme inhibitors, angiotensin receptor blockers and beta-blockers are most susceptible to the hypotensive nullifying effects of NSAIDs. Calcium channel blockers and centrally acting alpha-adrenertic agonists seem to be least affected. After antihypertensive drug therapy is initiated, patients return for follow-up and medication adjustments at least at monthly intervals until blood pressure goal is reached. Fewer than 50% of patients with hypertension will be controlled with a single drug. If blood pressure goals are not met, the clinician has three options for subsequent therapy, which include adding a second drug from another class, substituting an agent from another class, or increasing the dose of the initial drug. Combination therapies that include a diuretic are often effective, lessen the risk for side effects (by use of low doses of each component drug), and enhance adherence by simplification of the treatment program. Single agents that are approved by the FDA for the treatment of hypertension are located in a database in the artificial intelligence algorithm and identified by NDC code. Combination therapies approved by the FDA in the treatment of hypertension are available in fixed-combinations listed in the blockchain database as well. Because clinical practice guidelines and recent clinical trials, based on sound science and clinical evidence, have resulted in the designation of primary, secondary and tertiary status of particular categories of pharmacologic agents in the treatment of a multitude of diseases, an example of preferred single and combination agents used in the treatment of hypertension based on treatment guidelines is listed in the drug database as well. Treatment decisions for the patient are based on the characteristics of the patient as well as the characteristics of the pharmacologic agent(s) in question. The blockchain database will house the preferred, secondary, and tertiary drug choices for a patient with a primary diagnosis of hypertension, as well as a secondary diagnosis of diabetes mellitus type II, as defined by their separate ICD-10 CM coding. The methodology allows the calculation of the drug costs associated with the treatment of both hypertension and diabetes. In each separate disease state the choices of single or multiple pharmacologic agent(s), tablet strength(s), dosing schedule(s), as well as other clinical factors in conjunction with an understanding of the severity of the disease state and the rate of disease progression, allow for the calculation of costs of the prescribed agents as well as the attribution of an allowance for risk of additional medications necessary to treat the disease over a fixed period of time In another embodiment of the present invention, a patient visits a physician or other healthcare provider that is within a consortium of partners which utilizes the present invention. The physician or healthcare provider's facility utilizes a medical contact card, similar to a debit bank card, or a mobile app to acknowledge that the patient, who is a member of the consortium, is present. The blockchain network then validates that the individual is who they claim to be, and funds are made available for payment. In one embodiment, the funds made available are in the form of a cryptocurrency token. In another embodiment, a picture identification card (photo ID), fingerprint scan, or retinal scan is required to verify the patient's identity. After the patient's identity is verified, the patient is able to allocate one or more parts of their health records which they want the physician or healthcare provider to be able to access and view. For example, a patient is visiting an optometrist, and allocates their ophthalmic history to be available to the optometrist. In one embodiment, the patient is able to view an application on a computing device which displays a menu of what health records are available for viewing. In one embodiment, the patient releases their healthcare data to a physician or healthcare provider by transferring a native cryptocurrency token. The patient is then seen by the physician or healthcare provider and receives the health service. The physician or healthcare provider has as smart contract with the consortium, which is stored on the blockchain, so the healthcare costs for the patient are fixed. After the patient receives the health service, the physician or healthcare provider updates the consortium's blockchain with the health records and health status of the patient, including service notes from the visit. The blockchain is validated and encrypted with the patient's health notes and payment. Finally, the blockchain activates the smart contract and pays the physician or healthcare provider with cryptocurrency into the virtual wallet of the physician or healthcare provider. This can be converted to other digital or physical currencies as seen fit. The transaction is immediate. In one embodiment, the blockchain database verifies the identity of a patient at the onset of a medical care visit and makes native cryptocurrency funds available for a payment related to the medical care visit, one or more parts of the healthcare data of the patient are allocated for viewing by one or more healthcare providers at the onset of the medical care visit, healthcare data of the patient is then updated on the blockchain database with health records and service notes from the medical care visit; and payment is automatically transferred according to the terms of the smart contract to the healthcare provider in the form of a native cryptocurrency immediately at the completion of the medical visit.

In another embodiment of the present invention, the patient is experiencing symptoms or a condition which is operable to be improved with the use of medical *cannabis*, phytocannabinoids, or a similar substance. In one embodiment, the condition is peripheral neuropathy, chronic pain, inflammation, and/or fibromyalgia. The artificial intelligence system is able to consider any medication(s) which the patient is currently taking and analyze the impact of that medication on medical *cannabis*, phytocannabinoids, or a similar substance, as well as the impact of medical *cannabis*, phytocannabinoids, or a similar substance on the medication(s) which the patient is currently taking. Based on this information, the artificial intelligence system creates a treatment plan for the patient which includes a specific amount of medical *cannabis*, phytocannabinoids, or a similar substance in a specific time period. It is recognized in the art that *cannabis* molecules, such as CBD, THC, CBG, and CBN typically experience a plateau effect in their impact on patients, meaning that once a certain dosage is crossed, such as 20 mg/dose, further incremental increases in dosage will likely not make a large positive difference for a patient, but in some cases will cause a large negative response, such as causing a hallucinogenic response. The treatment plan which includes medical *cannabis*, phytocannabinoids, or a similar substance is stored in a distributed ledger to inform future treatment recommendations. In one embodiment, the patient reports the impact of the dosage, which is stored in the distributed ledger, and is operable to improve future treatment recommendations by the artificial intelligence system.

In another embodiment, the artificial intelligence system is connected to a smart-home device which is operable to interact with the patient audibly, visibly, or both. The smart-home device is operable to detect side effects of disease-related issues, such as, but not limited to, slurred speech and nystagmus. For example, the artificial intelligence system uses the smart-home device to triage, screen, and monitor for symptoms of specific diseases, such as COVID-19. In another embodiment, the artificial intelligence system uses the smart-home device to monitor progression or remission of diseases as well as drug-related issues. In another embodiment, the artificial intelligence system uses other consumer devices, such as, but not limited to, smart phones and/or smart watches, to interact with the patient audibly, visibly, or both. Furthermore, connecting the artificial intelligence system with a smart-home device, smart phone, and/or smart watch supports the implementation of telehealth in order to decrease medical costs. The devices and artificial intelligence system are operable to pick up patient information every day, analyze this information, and better update physicians as to patient health, such that health visits are only scheduled when truly necessary. In one example, the artificial intelligence system is operable to recognize vocal biomarkers or deviations from a vocal baseline created by the artificial intelligence system from audio analysis of data received from the smart-home device or other consumer device. Other baselines include a coughing baseline which indicates a typical cough or range of coughs for a patient and a breathing baseline which indicates typical breathing for a patient including breathing during different positions or states such as sleeping, exercising, resting, etc. In another embodiment, the artificial intelligence system is operable to create a visual baseline, such as a visual baseline of a patient's face including eyes, mouth, certain areas of the face, etc. based on video and or photo imagery from a smart-home device or other consumer device.

It will be appreciated that some exemplary embodiments described herein may include one or more generic or specialized processors (or "processing devices") such as microprocessors, digital signal processors, customized processors and field programmable gate arrays (FPGAs) and unique stored program instructions (including both software and firmware) that control the one or more processors to implement, in conjunction with certain non-processor circuits, some, most, or all of the functions of the methods and/or systems described herein. Alternatively, some or all functions may be implemented by a state machine that has no stored program instructions, or in one or more application specific integrated circuits (ASICs), in which each function or some combinations of certain of the functions are implemented as custom logic. Of course, a combination of the two approaches may be used. Moreover, some exemplary embodiments may be implemented as a computer-readable storage medium having computer readable code stored thereon for programming a computer, server, appliance, device, etc. each of which may include a processor to perform methods as described and claimed herein. Examples of such computer-readable storage mediums include, but are not limited to, a hard disk, an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory), a Flash memory, and the like.

Embodiments of the subject matter and the functional operations described in this specification are able to be implemented in digital electronic circuitry, or in computer software, firmware, or hardware, including the structures disclosed in this specification and their structural equivalents, or in combinations of one or more of them. Embodiments of the subject matter described in this specification are able to be implemented as one or more computer program products, i.e., one or more modules of computer program instructions encoded on a tangible program carrier for execution by, or to control the operation of, data processing apparatus. The tangible program carrier is able to be a propagated signal or a computer readable medium. The propagated signal is an artificially generated signal, e.g., a machine generated electrical, optical, or electromagnetic signal that is generated to encode information for transmission to suitable receiver apparatus for execution by a computer. The computer readable medium is able to be a machine readable storage device, a machine readable storage substrate, a memory device, a composition of matter effecting a machine readable propagated signal, or a combination of one or more of them.

A computer program (also known as a program, software, software application, application, script, or code) is operable to be written in any form of programming language, including compiled or interpreted languages, or declarative or procedural languages, and it is able to be deployed in any form, including as a standalone program or as a module, component, subroutine, or other unit suitable for use in a computing environment. A computer program does not necessarily correspond to a file in a file system. A program is operable be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program is operable be deployed to be executed on one computer or on multiple computers that are located at one site or distributed across multiple sites and interconnected by a communication network.

Additionally, the logic flows and structure block diagrams described in this patent document, which describe particular methods and/or corresponding acts in support of steps and corresponding functions in support of disclosed structural means, may also be utilized to implement corresponding software structures and algorithms, and equivalents thereof. The processes and logic flows described in this specification are able to be performed by one or more programmable processors (computing device processors) executing one or more computer applications or programs to perform functions by operating on input data and generating output.

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, solid state drives, or optical disks. However, a computer need not have such devices.

Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD ROM disks. The processor and the memory are able to be supplemented by, or incorporated in, special purpose logic circuitry.

To provide for interaction with a user, embodiments of the subject matter described in this specification are operable to be implemented on a computer having a display device, e.g., a CRT (cathode ray tube) or LCD (liquid crystal display) monitor, for displaying information to the user and a keyboard and a pointing device, e.g., a mouse or a trackball, by which the user is able to provide input to the computer. Other kinds of devices are operable be used to provide for interaction with a user as well; for example, feedback provided to the user is operable to be any form of sensory feedback, e.g., visual feedback, auditory feedback, or tactile feedback; and input from the user is able to be received in any form, including acoustic, speech, or tactile input.

Embodiments of the subject matter described in this specification are operable to be implemented in a computing system that includes a back end component, e.g., as a data server, or that includes a middleware component, e.g., an application server, or that includes a front end component, e.g., a client computer having a graphical user interface or a Web browser through which a user is able to interact with an implementation of the subject matter described is this specification, or any combination of one or more such back end, middleware, or front end components. The components of the system are able to be interconnected by any form or medium of digital data communication, e.g., a communication network. Examples of communication networks include a local area network ("LAN") and a wide area network ("WAN"), e.g., the Internet.

The computing system is operable to include clients and servers. A client and server are generally remote from each other and typically interact through a communication network or the cloud. The relationship of client and server arises by virtue of computer programs running on the respective computers and having a client server relationship to each other.

Further, many embodiments are described in terms of sequences of actions to be performed by, for example, elements of a computing device. It will be recognized that various actions described herein are operable to be performed by specific circuits (e.g., application specific integrated circuits (ASICs)), by program instructions being executed by one or more processors, or by a combination of both. Additionally, these sequences of actions described herein are operable to be considered to be embodied entirely within any form of computer readable storage medium having stored therein a corresponding set of computer instructions that upon execution would cause an associated processor to perform the functionality described herein. Thus, the various aspects of the invention may be embodied in a number of different forms, all of which have been contemplated to be within the scope of the claimed subject matter. In addition, for each of the embodiments described herein, the corresponding form of any such embodiments may be described herein as, for example, "logic configured to" perform the described action.

The computer system may also include a main memory, such as a random access memory (RAM) or other dynamic storage device (e.g., dynamic RAM (DRAM), static RAM (SRAM), and synchronous DRAM (SDRAM)), coupled to the bus for storing information and instructions to be executed by processor. In addition, the main memory may be used for storing temporary variables or other intermediate information during the execution of instructions by the processor. The computer system may further include a read only memory (ROM) or other static storage device (e.g., programmable ROM (PROM), erasable PROM (EPROM), and electrically erasable PROM (EEPROM)) coupled to the bus for storing static information and instructions for the processor.

The computer system may also include a disk controller coupled to the bus to control one or more storage devices for storing information and instructions, such as a magnetic hard disk, and a removable media drive (e.g., floppy disk drive, read-only compact disc drive, read/write compact disc drive, compact disc jukebox, tape drive, and removable magneto-optical drive). The storage devices may be added to the computer system using an appropriate device interface (e.g., small computer system interface (SCSI), integrated device electronics (IDE), enhanced-IDE (E-IDE), direct memory access (DMA), or ultra-DMA).

The computer system may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

The computer system may also include a display controller coupled to the bus to control a display, such as a cathode ray tube (CRT), liquid crystal display (LCD) or any other type of display, for displaying information to a computer user. The computer system may also include input devices, such as a keyboard and a pointing device, for interacting with a computer user and providing information to the processor. Additionally, a touch screen could be employed in conjunction with display. The pointing device, for example, may be a mouse, a trackball, or a pointing stick for communicating direction information and command selections to the processor and for controlling cursor movement on the display. In addition, a printer may provide printed listings of data stored and/or generated by the computer system.

The computer system performs a portion or all of the processing steps of the invention in response to the processor executing one or more sequences of one or more instructions contained in a memory, such as the main memory. Such instructions may be read into the main memory from another computer readable medium, such as a hard disk or a removable media drive. One or more processors in a multi-processing arrangement may also be employed to execute the sequences of instructions contained in main memory. In alternative embodiments, hard-wired circuitry may be used in place of or in combination with software instructions. Thus, embodiments are not limited to any specific combination of hardware circuitry and software.

As stated above, the computer system includes at least one computer readable medium or memory for holding instructions programmed according to the teachings of the invention and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, punch cards, paper tape, or other physical medium with patterns of holes, a carrier wave (described below), or any other medium from which a computer is able to read.

Stored on any one or on a combination of computer readable media, the present invention includes software for controlling the computer system, for driving a device or devices for implementing the invention, and for enabling the computer system to interact with a human user. Such software may include, but is not limited to, device drivers, operating systems, development tools, and applications software. Such computer readable media further includes the computer program product of the present invention for performing all or a portion (if processing is distributed) of the processing performed in implementing the invention.

The computer code or software code of the present invention may be any interpretable or executable code mechanism, including but not limited to scripts, interpretable programs, dynamic link libraries (DLLs), Java classes, and complete executable programs. Moreover, parts of the processing of the present invention may be distributed for better performance, reliability, and/or cost.

Various forms of computer readable media may be involved in carrying out one or more sequences of one or more instructions to processor for execution. For example, the instructions may initially be carried on a magnetic disk of a remote computer. The remote computer is able to load the instructions for implementing all or a portion of the present invention remotely into a dynamic memory and send the instructions over the air (e.g. through a wireless cellular network or WiFi network). A modem local to the computer system may receive the data over the air and use an infrared transmitter to convert the data to an infrared signal. An infrared detector coupled to the bus is able to receive the data carried in the infrared signal and place the data on the bus. The bus carries the data to the main memory, from which the processor retrieves and executes the instructions. The instructions received by the main memory may optionally be stored on storage device either before or after execution by processor.

The computer system also includes a communication interface coupled to the bus. The communication interface provides a two-way data communication coupling to a network link that is connected to, for example, a local area network (LAN), or to another communications network such as the Internet. For example, the communication interface may be a network interface card to attach to any packet switched LAN. As another example, the communication interface may be an asymmetrical digital subscriber line (ADSL) card, an integrated services digital network (ISDN) card or a modem to provide a data communication connection to a corresponding type of communications line. Wireless links may also be implemented. In any such implementation, the communication interface sends and receives electrical, electromagnetic or optical signals that carry digital data streams representing various types of information.

The network link typically provides data communication to the cloud through one or more networks to other data devices. For example, the network link may provide a connection to another computer or remotely located presentation device through a local network (e.g., a LAN) or through equipment operated by a service provider, which provides communication services through a communications network. In preferred embodiments, the local network and the communications network preferably use electrical, electromagnetic, or optical signals that carry digital data streams. The signals through the various networks and the signals on the network link and through the communication interface, which carry the digital data to and from the computer system, are exemplary forms of carrier waves transporting the information. The computer system is operable to transmit and receive data, including program code, through the network(s) and, the network link and the communication interface. Moreover, the network link may provide a connection through a LAN to a client device or client device such as a personal digital assistant (PDA), laptop computer, tablet computer, smartphone, or cellular telephone. The LAN communications network and the other communications networks such as cellular wireless and wife networks may use electrical, electromagnetic or optical signals that carry digital data streams. The processor system is operable to transmit notifications and receive data, including program code, through the network(s), the network link and the communication interface.

FIG. 8 is a schematic diagram of an embodiment of the invention illustrating a computer system, generally described as 800, having a network 810, a plurality of computing devices 820, 830, 840, a server 850, and a database 870.

The server 850 is constructed, configured, and coupled to enable communication over a network 810 with a plurality of computing devices 820, 830, 840. The server 850 includes a processing unit 851 with an operating system 852. The operating system 852 enables the server 850 to communicate through network 810 with the remote, distributed user devices. Database 870 is operable to house an operating system 872, memory 874, and programs 876.

In one embodiment of the invention, the system 800 includes a network 810 for distributed communication via a wireless communication antenna 812 and processing by at least one mobile communication computing device 830. Alternatively, wireless and wired communication and connectivity between devices and components described herein include wireless network communication such as WI-FI, WORLDWIDE INTEROPERABILITY FOR MICROWAVE ACCESS (WIMAX), Radio Frequency (RF) communication including RF identification (RFID), NEAR FIELD COMMUNICATION (NFC), BLUETOOTH including BLUETOOTH LOW ENERGY (BLE), ZIGBEE, Infrared (IR) communication, cellular communication, satellite communication, Universal Serial Bus (USB), Ethernet communications, communication via fiber-optic cables, coaxial cables, twisted pair cables, and/or any other type of wireless or wired communication. In another embodiment of the invention, the system 800 is a virtualized computing system capable of executing any or all aspects of software and/or application components presented herein on the computing devices 820, 830, 840. In certain aspects, the computer system 800 is operable to be implemented using hardware or a combination of software and hardware, either in a dedicated computing device, or integrated into another entity, or distributed across multiple entities or computing devices.

By way of example, and not limitation, the computing devices 820, 830, 840 are intended to represent various forms of electronic devices including at least a processor and a memory, such as a server, blade server, mainframe, mobile phone, personal digital assistant (PDA), smartphone, desktop computer, netbook computer, tablet computer, workstation, laptop, and other similar computing devices. The components shown here, their connections and relationships, and their functions, are meant to be exemplary only, and are not meant to limit implementations of the invention described and/or claimed in the present application.

In one embodiment, the computing device 820 includes components such as a processor 860, a system memory 862 having a random access memory (RAM) 864 and a read-only memory (ROM) 866, and a system bus 868 that couples the memory 862 to the processor 860. In another embodiment, the computing device 830 is operable to additionally include components such as a storage device 890 for storing the operating system 892 and one or more application programs 894, a network interface unit 896, and/or an input/output controller 898. Each of the components is operable to be coupled to each other through at least one bus 868. The input/output controller 898 is operable to receive and process input from, or provide output to, a number of other devices 899, including, but not limited to, alphanumeric input devices, mice, electronic styluses, display units, touch screens, signal generation devices (e.g., speakers), or printers.

By way of example, and not limitation, the processor 860 is operable to be a general-purpose microprocessor (e.g., a central processing unit (CPU)), a graphics processing unit (GPU), a microcontroller, a Digital Signal Processor (DSP), an Application Specific Integrated Circuit (ASIC), a Field Programmable Gate Array (FPGA), a Programmable Logic Device (PLD), a controller, a state machine, gated or transistor logic, discrete hardware components, or any other suitable entity or combinations thereof that is able to perform calculations, process instructions for execution, and/or other manipulations of information.

In another implementation, shown as 840 in FIG. 8, multiple processors 860 and/or multiple buses 868 are operable to be used, as appropriate, along with multiple memories 862 of multiple types (e.g., a combination of a DSP and a microprocessor, a plurality of microprocessors, one or more microprocessors in conjunction with a DSP core).

Also, multiple computing devices are operable to be connected, with each device providing portions of the necessary operations (e.g., a server bank, a group of blade servers, or a multi-processor system). Alternatively, some steps or methods are operable to be performed by circuitry that is specific to a given function.

According to various embodiments, the computer system 800 is operable to operate in a networked environment using logical connections to local and/or remote computing devices 820, 830, 840 through a network 810. A computing device 830 is operable to connect to a network 810 through a network interface unit 896 connected to a bus 868. Computing devices are operable to communicate communication media through wired networks, direct-wired connections or wirelessly, such as acoustic, RF, or infrared, through an antenna 897 in communication with the network antenna 812 and the network interface unit 896, which are operable to include digital signal processing circuitry when necessary. The network interface unit 896 is operable to provide for communications under various modes or protocols.

In one or more exemplary aspects, the instructions are operable to be implemented in hardware, software, firmware, or any combinations thereof. A computer readable medium is operable to provide volatile or non-volatile storage for one or more sets of instructions, such as operating systems, data structures, program modules, applications, or other data embodying any one or more of the methodologies or functions described herein. The computer readable medium is operable to include the memory 862, the processor 860, and/or the storage media 890 and is operable be a single medium or multiple media (e.g., a centralized or distributed computer system) that store the one or more sets of instructions 900. Non-transitory computer readable media includes all computer readable media, with the sole exception being a transitory, propagating signal per se. The instructions 900 are further operable to be transmitted or received over the network 810 via the network interface unit 896 as communication media, which is operable to include a modulated data signal such as a carrier wave or other transport mechanism and includes any delivery media. The term "modulated data signal" means a signal that has one or more of its characteristics changed or set in a manner as to encode information in the signal.

Storage devices 890 and memory 862 include, but are not limited to, volatile and non-volatile media such as cache, RAM, ROM, EPROM, EEPROM, FLASH memory, or other solid state memory technology; discs (e.g., digital versatile discs (DVD), HD-DVD, BLU-RAY, compact disc (CD), or CD-ROM) or other optical storage; magnetic cassettes, magnetic tape, magnetic disk storage, floppy disks, or other magnetic storage devices; or any other medium that is able to store the computer readable instructions and which is able to be accessed by the computer system 800.

In one embodiment, the computer system 800 is within a cloud-based network. In one embodiment, the server 850 is a designated physical server for distributed computing devices 820, 830, and 840. In one embodiment, the server 850 is a cloud-based server platform. In one embodiment, the cloud-based server platform hosts serverless functions for distributed computing devices 820, 830, and 840.

In another embodiment, the computer system 800 is within an edge computing network. The server 850 is an edge server, and the database 870 is an edge database. The edge server 850 and the edge database 870 are part of an edge computing platform. In one embodiment, the edge server 850 and the edge database 870 are designated to distributed computing devices 820, 830, and 840. In one embodiment, the edge server 850 and the edge database 870 are not designated for distributed computing devices 820, 830, and 840. The distributed computing devices 820, 830, and 840 connect to an edge server in the edge computing network based on proximity, availability, latency, bandwidth, and/or other factors.

It is also contemplated that the computer system 800 is operable to not include all of the components shown in FIG. 8, is operable to include other components that are not explicitly shown in FIG. 8, or is operable to utilize an architecture completely different than that shown in FIG. 8. The various illustrative logical blocks, modules, elements, circuits, and algorithms described in connection with the embodiments disclosed herein are operable to be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application (e.g., arranged in a different order or partitioned in a different way), but such implementation decisions should not be interpreted as causing a departure from the scope of the present invention.

The above-mentioned examples are provided to serve the purpose of clarifying the aspects of the invention, and it will be apparent to one skilled in the art that they do not serve to limit the scope of the invention. By nature, this invention is highly adjustable, customizable and adaptable. The above-mentioned examples are just some of the many configurations that the mentioned components are able to take on. All modifications and improvements have been deleted herein for the sake of conciseness and readability but are properly within the scope of the present invention.

The invention claimed is:

1. A method for making artificial intelligence based medical treatment plan recommendations comprising the steps of:
   providing an electronic device including a processor and an artificial intelligence system;
   storing healthcare data of a patient in a blockchain database, wherein the healthcare data of the patient includes one or more existing conditions and one or more conditions not previously present in a therapy regime of the patient, one or more limiting factors, and a compliance record for the existing condition;
   wherein the one or more limiting factors includes existing drugs and therapies of the patient, lifestyle behaviors of the patient, and any other information which limits the ability of the patient to access or complete a therapy;
   retrieving the healthcare data of the patient from the blockchain database;
   the artificial intelligence system determining a therapeutic behavior pattern of the patient utilizing a combination of the compliance record for the existing condition and the one or more limiting factors;
   the artificial intelligence system determining one or more therapies for the one or more conditions not previously present in the therapy regime of the patient based on the healthcare data of the patient;
   the artificial intelligence system ranking the one or more therapies based on the likelihood of the therapy treating the one or more existing conditions and the one or more conditions not previously present in the therapy regime of the patient based on the compliance record and the one or more limiting factors;
   the artificial intelligence system determining one or more cost quotes for the one or more therapies and displaying the one or more cost quotes;
   receiving selection of a not yet implemented therapy and a cost quote for the selected not yet implemented therapy by a user;
   the blockchain database creating a smart contract for the execution of the selected not yet implemented therapy;
   one or more parts of the healthcare data of the patient being allocated for viewing by one or more healthcare providers at the onset of a medical care visit;
   updating the healthcare data of the patient on the blockchain database with health records and service notes from the medical care visit; and
   automatically transferring payment according to the terms of the smart contract to a healthcare provider in the form of a native cryptocurrency immediately at the completion of the medical visit.

2. The method of claim 1, wherein the one or more existing conditions and/or the one or more conditions not previously present in the therapy regime of the patient are identified with an ICD-10 code and the one or more therapies includes a prescription drug which is identified with a National Drug Code.

3. The method of claim 1, wherein access to the healthcare data of a patient is controlled by the patient, and wherein the healthcare data of a patient is retrieved from the blockchain database in exchange for a native cryptocurrency.

4. The method of claim 1, further comprising calculating, by the artificial intelligence system, a probability of disease progression for the one or more existing conditions and/or the one or more conditions not previously present in the therapy regime of the patient with the selected not yet implemented therapy and a probability of disease progression for the one or more existing conditions and/or the one or more conditions not previously present in the therapy regime of the patient without the selected therapy.

5. The method of claim 1, further comprising automatically retraining the artificial intelligence system upon addition of new healthcare data to the blockchain database.

6. The method of claim 1, wherein determining one or more therapies for the one or more conditions not previously present in the therapy regime of the patient further comprises analyzing the influence of one or more comorbidities, analyzing the interactions between two or more medications and side effects of the combination of two or more medications, or analyzing possible side effects of the one or more therapies.

7. The method of claim 1, wherein the one or more therapies include a laboratory test, a medical device, a digital health technology, a prescriptive drug, medical *cannabis*, a surgical procedure, a phytocannabinoid, and a terpenoid molecule.

8. The method of claim 1, further comprising:
   wherein the selected not yet implemented therapy comprises a prescriptive drug;

receiving submissions from one or more pharmacies to dispense the prescriptive drug;

storing the submissions on the blockchain database;

receiving a selection by a user, of a pharmacy of the one or pharmacies to dispense the prescriptive drug;

the selected pharmacy dispensing the prescriptive drug to the patient; and recording the dispensing of the prescriptive drug on the blockchain database.

9. A method for making artificial intelligence based medical treatment plan recommendations comprising the steps of:

providing an electronic device including a processor and an artificial intelligence system;

storing healthcare data of a patient in a blockchain database, wherein the healthcare data of the patient includes one or more existing conditions and one or more conditions not previously present in a therapy regime of the patient;

retrieving the healthcare data of the patient from the blockchain database;

the artificial intelligence system determining one or more therapies based on the healthcare data of the patient, wherein the artificial intelligence system takes into account a therapeutic behavior pattern of the patient based on a compliance record of the patient, at least one limiting factor, and at least one other medical condition of the patient;

wherein the at least one limiting factor includes existing drugs and therapies of the patient, lifestyle behaviors of the patient, and any other information which limits the ability of the patient to access or complete a therapy;

the artificial intelligence system calculating a probability of disease progression for the one or more existing conditions and the one or more conditions not previously present in the therapy regime of the patient;

where more than one therapy option exists, the artificial intelligence system ranking the more than one therapies by an ability of the more than one therapies to cure, remedy, alleviate, or otherwise cause the one or more conditions not previously present in the therapy regime of the patient to go into remission so that the one or more conditions not previously present in the therapy regime of the patient would be clinically assessed to be under control or resolved based on the compliance record of the patient, the at least one limiting factor, and the at least one other medical condition of the patient;

the artificial intelligence system determining one or more cost quotes for the one or more therapies and displaying the one or more cost quotes;

receiving a selection of a not yet implemented therapy and a cost quote for the selected not yet implemented therapy by a user;

the blockchain database creating a smart contract for the execution of the selected not yet implemented therapy;

wherein the blockchain database is operable to accept native and third-party cryptocurrencies as payment for the selected not yet implemented therapy;

one or more parts of the healthcare data of the patient being allocated for viewing by one or more healthcare providers at the onset of a medical care visit;

updating the healthcare data of the patient on the blockchain database with health records and service notes from the medical care visit; and automatically transferring payment according to the terms of the smart contract to a healthcare provider in the form of a native cryptocurrency immediately at the completion of the medical visit.

10. The method of claim 9, wherein the selected not yet implemented therapy comprises a prescriptive drug, further comprising receiving submissions from one or more pharmacies to dispense the prescriptive drug, receiving a selection of a pharmacy of the one or pharmacies to dispense the prescriptive drug, and storing the selection of the pharmacy with the smart contract in the blockchain database.

11. The method of claim 9, wherein access to the healthcare data of a patient is controlled by the patient, and wherein the healthcare data of a patient is retrieved from the blockchain database in exchange for a native cryptocurrency.

12. The method of claim 9, wherein the one or more existing conditions and/or one or more conditions not previously present in the therapy regime of the patient are identified with an ICD-10 code and the one or more therapies includes a prescription drug which is identified with a National Drug Code.

13. The method of claim 9, wherein the smart contract is executed upon a transfer of a native cryptocurrency.

14. The method of claim 9, wherein the one or more therapies include a laboratory test, a medical device, a digital health technology, a prescriptive drug, medical *cannabis*, a surgical procedure, a phytocannabinoid, and a terpenoid molecule.

15. A system for making artificial intelligence based medical treatment plan recommendations comprising:

an electronic device including a processor and an artificial intelligence system; and a blockchain database including healthcare data of a patient, wherein the healthcare data of a patient includes one or more existing conditions, one or more limiting factors, and a compliance record the for the existing condition, and one or more conditions not previously present in a therapy regime of the patient;

wherein the one or more limiting factors includes existing drugs and therapies of the patient, lifestyle behaviors of the patient, and any other information which limits the ability of the patient to access or complete a therapy;

wherein the artificial intelligence system determines one or more therapies for the one or more conditions not previously present in the therapy regime of the patient based on the healthcare data of the patient;

wherein the artificial intelligence system receives the healthcare data of the patient and determines at least one not yet implemented therapy based on the healthcare data of the patient for the one or more conditions not previously present in the therapy regime of the patient;

wherein the artificial intelligence system ranks the one or more therapies based on the likelihood of the therapy treating the one or more existing conditions and the one or more conditions not previously present in the therapy regime of the patient based on the compliance record and the one or more limiting factors;

wherein the artificial intelligence system calculates a probability of disease progression for the one or more existing conditions and the one or more conditions not previously present in the therapy regime of the patient;

wherein the artificial intelligence system determines at least one cost quote for the at least one not yet implemented therapy and displays the at least one cost quote;

wherein the blockchain database creates at least one smart contract for the at least one not yet implemented therapy;
one or more parts of the healthcare data of the patient being allocated for viewing by one or more healthcare providers at the onset of a medical care visit;
updating the healthcare data of the patient on the blockchain database with health records and service notes from the medical care visit; and
automatically transferring payment according to the terms of the smart contract to a healthcare provider in the form of a native cryptocurrency immediately at the completion of the medical visit.

16. The system of claim 15, wherein a cryptocurrency token is transferred as payment for the patient to receive the at least one not yet implemented therapy.

17. The system of claim 15, wherein the at least one not yet implemented therapy comprises a first therapy option and a second therapy option, and wherein the first possible therapy option and the second possible therapy option are ranked based on probability of being a successful treatment based on factors including the patient's treatment compliance history, cost of the first possible therapy option and the second possible therapy option, and historical success rate of the first possible therapy option and the second possible therapy option as determined from information stored on the blockchain database.

18. The system of claim 15, wherein the at least one smart contract is stored in the blockchain database, and wherein the smart contract is executed upon a transfer of a native or a third-party cryptocurrency.

19. The system of claim 15, wherein the at least one not yet implemented therapy comprises a prescriptive drug, wherein the system receives submissions from one or more pharmacies to dispense the prescriptive drug, and wherein the system receives a selection by a user, of a pharmacy of the one or pharmacies to dispense the prescriptive drug, and the selection of the pharmacy is stored with the at least one smart contract in the blockchain database.

\* \* \* \* \*